US010004460B2

(12) United States Patent
Banet et al.

(10) Patent No.: US 10,004,460 B2
(45) Date of Patent: Jun. 26, 2018

(54) FLOORMAT PHYSIOLOGICAL SENSOR

(71) Applicant: TOSENSE, INC., La Jolla, CA (US)

(72) Inventors: Matthew Banet, San Diego, CA (US); Marshal Singh Dhillon, San Diego, CA (US); Susan Meeks Pede, Encinitas, CA (US); Lauren Nicole Miller Hayward, San Diego, CA (US); Arthur Deptala, Santee, CA (US); Jonas Dean Cochran, Santee, CA (US)

(73) Assignee: TOSENSE, INC., San Diego, CA (US)

( * ) Notice: Subject to any disclaimer, the term of this patent is extended or adjusted under 35 U.S.C. 154(b) by 25 days.

(21) Appl. No.: 14/988,663

(22) Filed: Jan. 5, 2016

(65) Prior Publication Data

US 2017/0188958 A1 Jul. 6, 2017

(51) Int. Cl.
| | |
|---|---|
| *A61B 5/0205* | (2006.01) |
| *A61B 5/00* | (2006.01) |
| *A61B 5/022* | (2006.01) |
| *A61B 5/1455* | (2006.01) |
| *A61B 5/0245* | (2006.01) |
| *A61B 5/024* | (2006.01) |

(52) U.S. Cl.
CPC ............ *A61B 5/6892* (2013.01); *A61B 5/022* (2013.01); *A61B 5/0245* (2013.01); *A61B 5/02444* (2013.01); *A61B 5/14552* (2013.01)

(58) Field of Classification Search
CPC ... A61B 5/6892; A61B 5/0402; A61B 5/0456; A61B 5/02125
See application file for complete search history.

(56) References Cited

U.S. PATENT DOCUMENTS

2013/0310700 A1* 11/2013 Wiard ................ A61B 5/02125
600/485
2016/0374618 A1* 12/2016 Giovangrandi ...... A61B 5/6887
600/393

FOREIGN PATENT DOCUMENTS

WO 2008154647 A1 12/2008

OTHER PUBLICATIONS

Anand et al., Monitoring Changes in Fluid Status With a Wireless Multisensor Monitor: Results From the Fluid Removal During Adherent Renal Monitoring (FARM) Study. Congest Heart Fail. Jan.-Feb. 2012;18(1):32-36.

(Continued)

*Primary Examiner* — George Evanisko
(74) *Attorney, Agent, or Firm* — Acuity Law Group, PC; Michael A. Whittaker

(57) ABSTRACT

A stand-on physiological sensor (e.g. floormat) measures vital signs and various hemodynamic parameters, including blood pressure and ECG waveforms. The sensor is similar in configuration to a common bathroom scale and includes electrodes that take electrical measurements from a patient's feet to generate bioimpedance waveforms, which are analyzed digitally to extract various other parameters, as well as a cuff-type blood pressure system that takes physical blood pressure measurements at one of the patient's feet. Blood pressure can also be calculated/derived from the bioimpedance waveforms. Measured parameters are transmitted wirelessly to facilitate remote monitoring of the patient for heart failure, chronic heart failure, end-stage renal disease, cardiac arrhythmias, and other degenerative diseases.

29 Claims, 15 Drawing Sheets

(56) References Cited

OTHER PUBLICATIONS

Bernstein, Impedance Cardiography, Pulsatile blood flow and the biophysical and electrodynamic basis for the stroke volume equations. J Electr Bioimp, 2010;1: 2-17.
Harley et al., Pressure-Flow Studies in Man. An Evaluation of the Duration of the Phases of Systole. J Clin Invest. May 1969;48(5):895-905.
Jacques et al., Pulse pressure variation and stroke vol. variation during increased intra-abdominal pressure: an experimental study. Crit Care. 2011;15(1):R33 (9 pages).
Macias et al., Body fat measurement by bioelectrical impedance and air displacement plethysmography: a cross-validation study to design bioelectrical impedance equations in Mexican adults. Nutr J. Aug. 15, 2007;6:18 (7 pages).
Packer et al., Utility of Impedance Cardiography for the Identification of Short-Term Risk of Clinical Decompensation in Stable Patients With Chronic Heart Failure. J Am Coll Cardiol. Jun. 6, 2006:47(11):2245-2252.

* cited by examiner

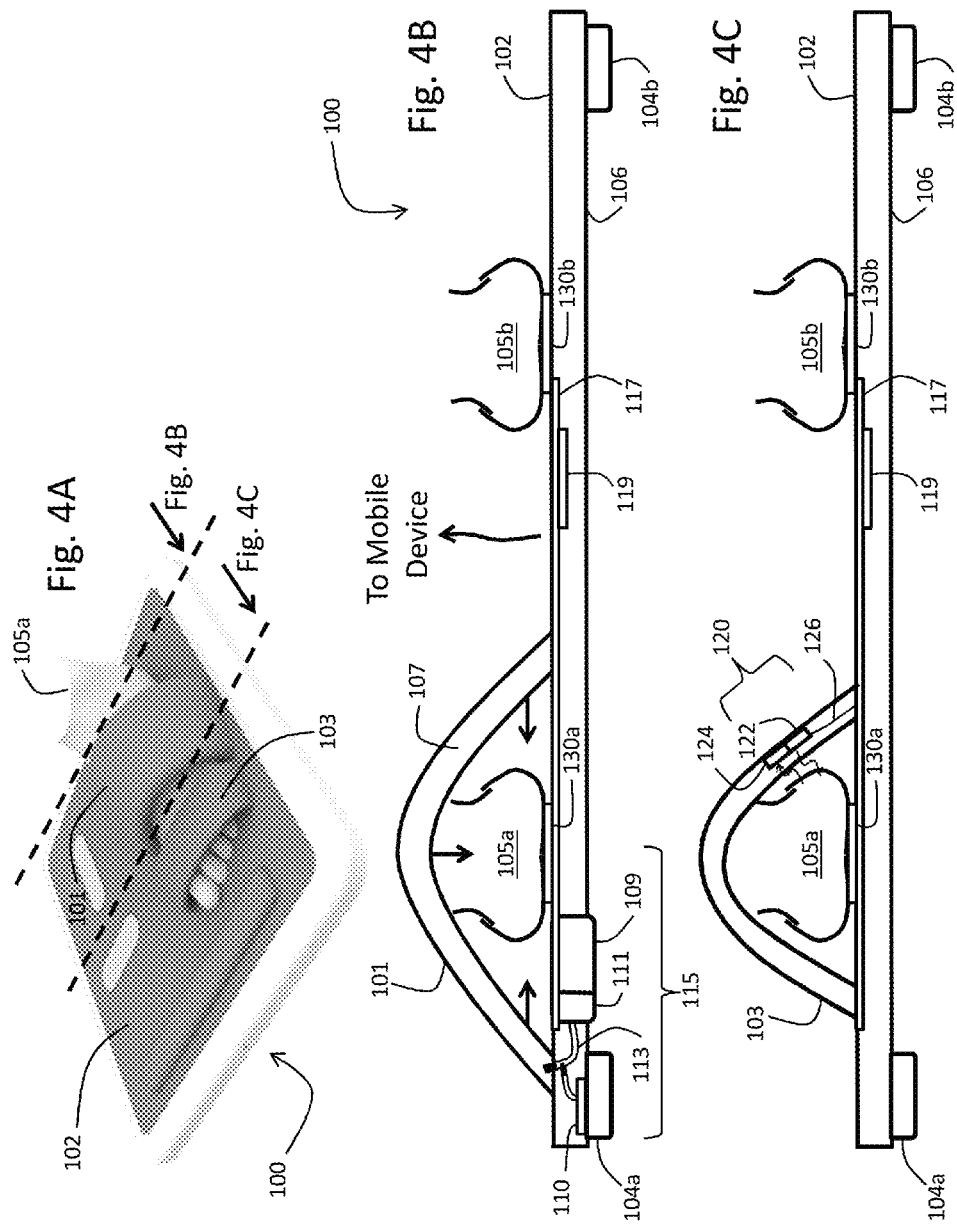

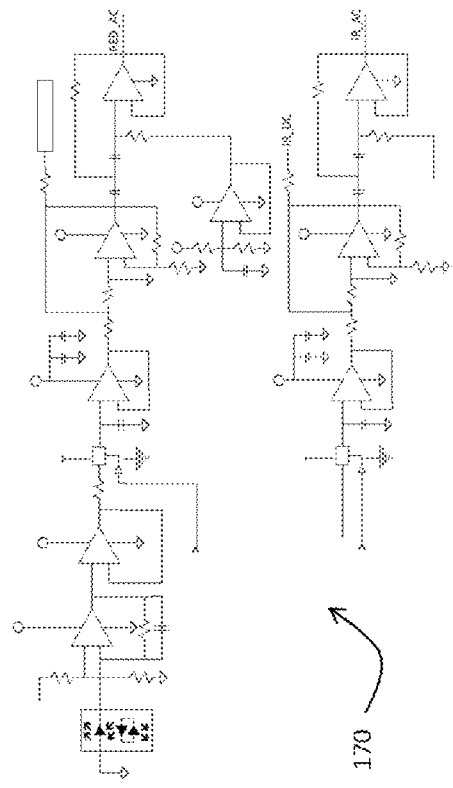
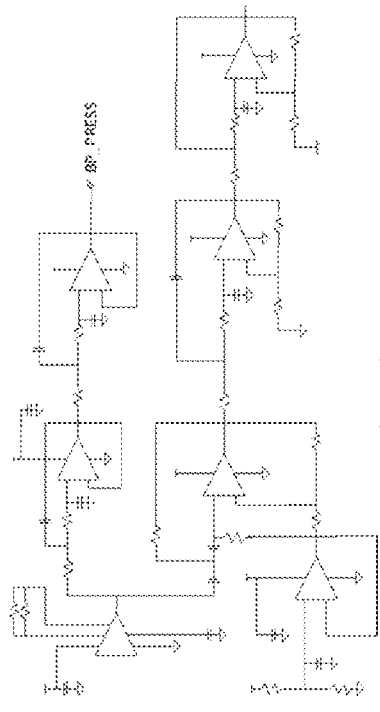
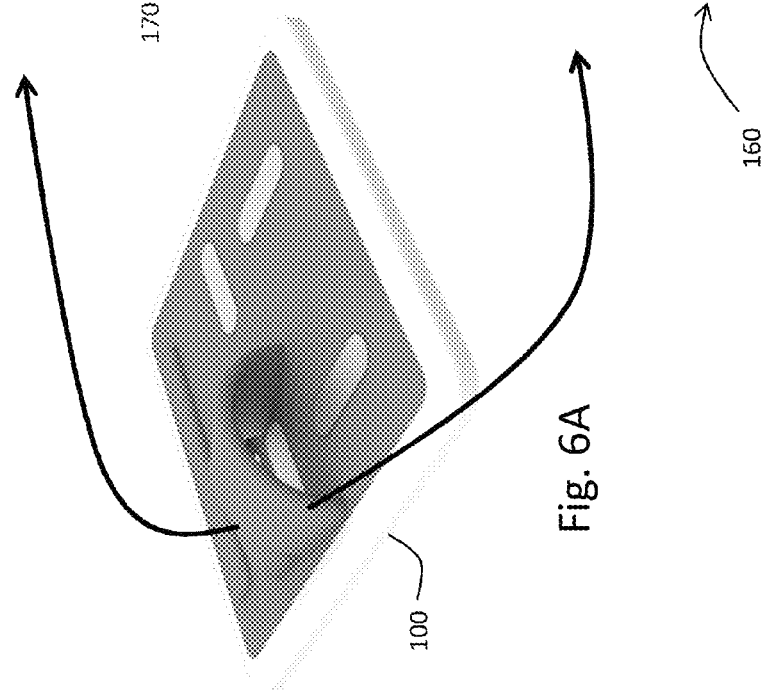
Fig. 6C
Fig. 6B
Fig. 6A

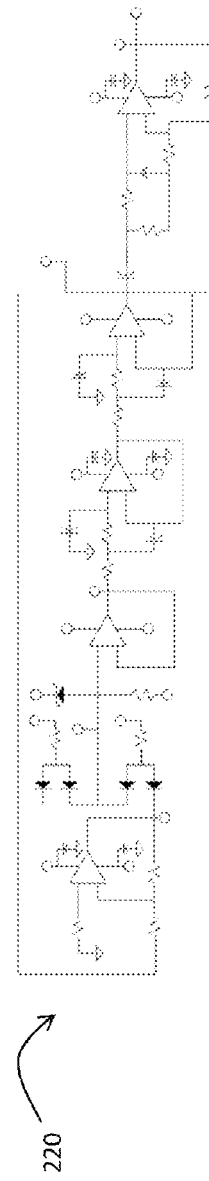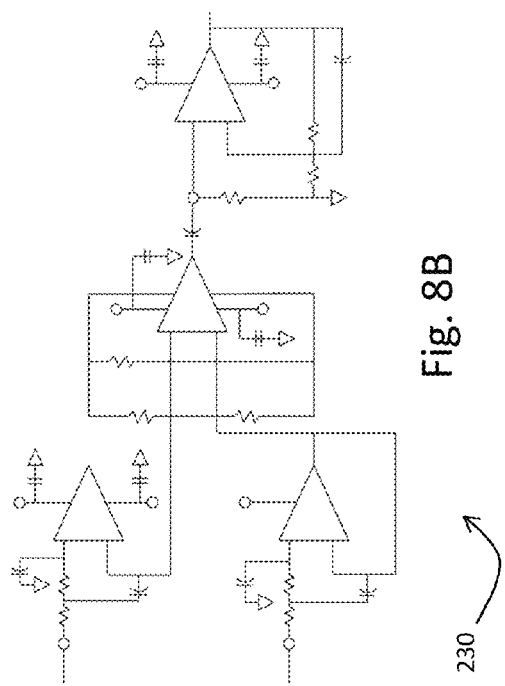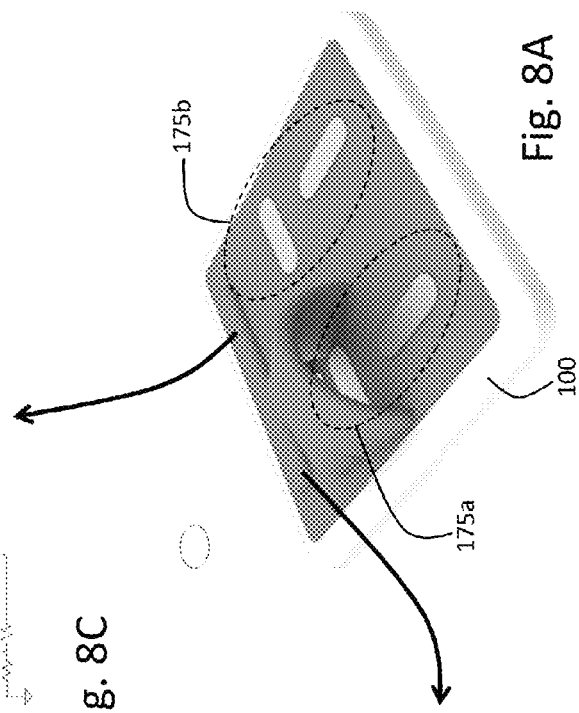

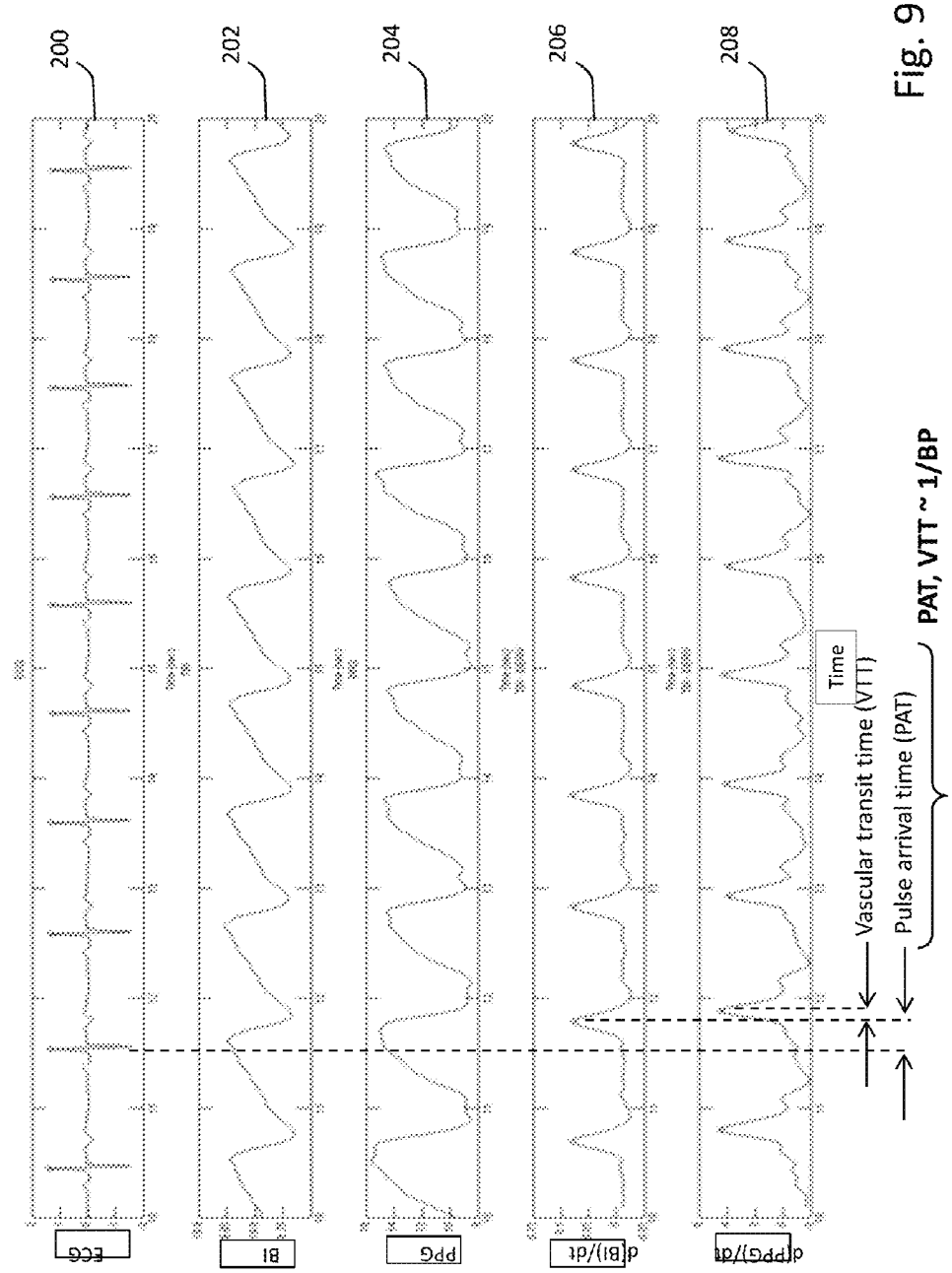

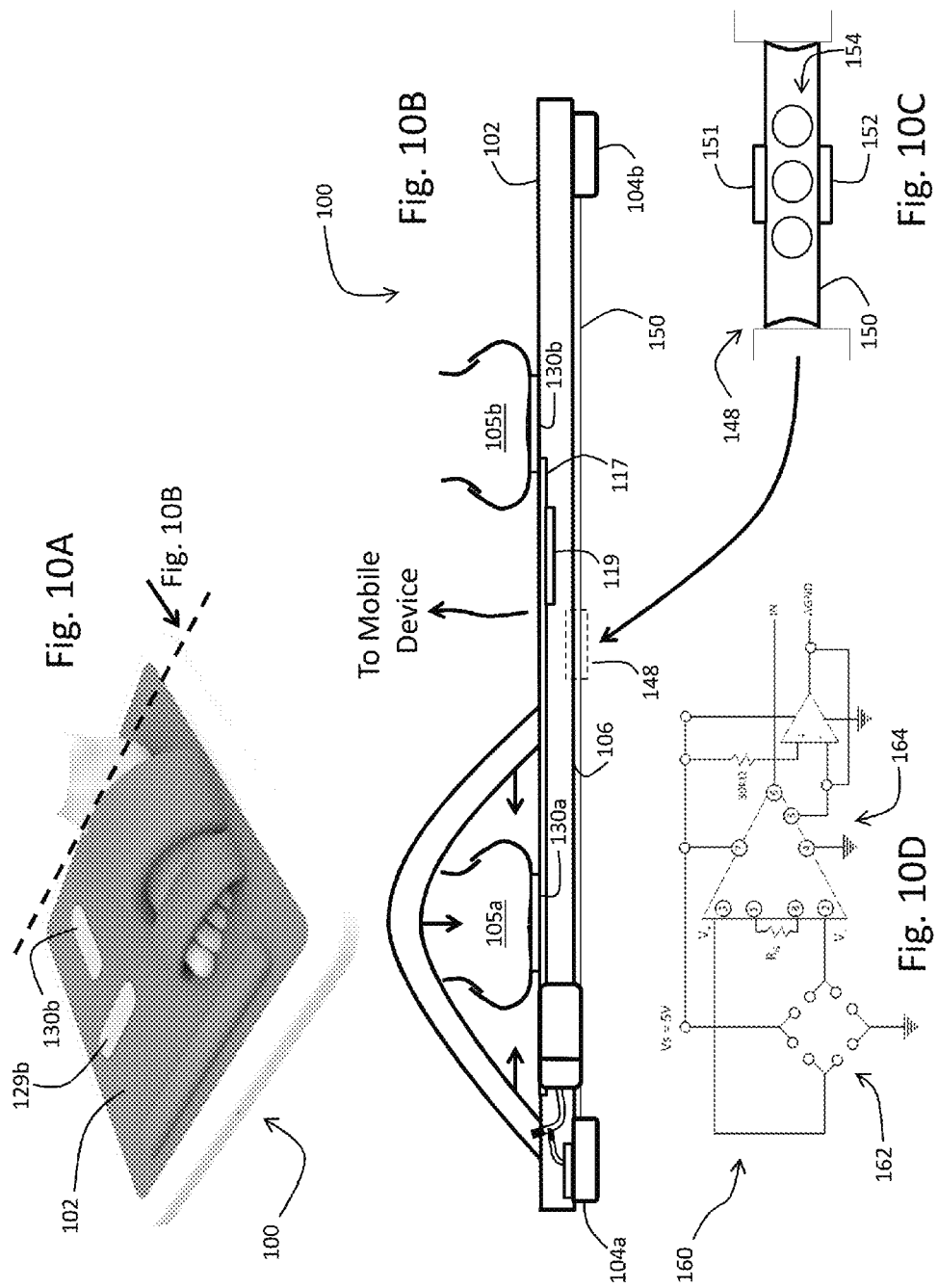

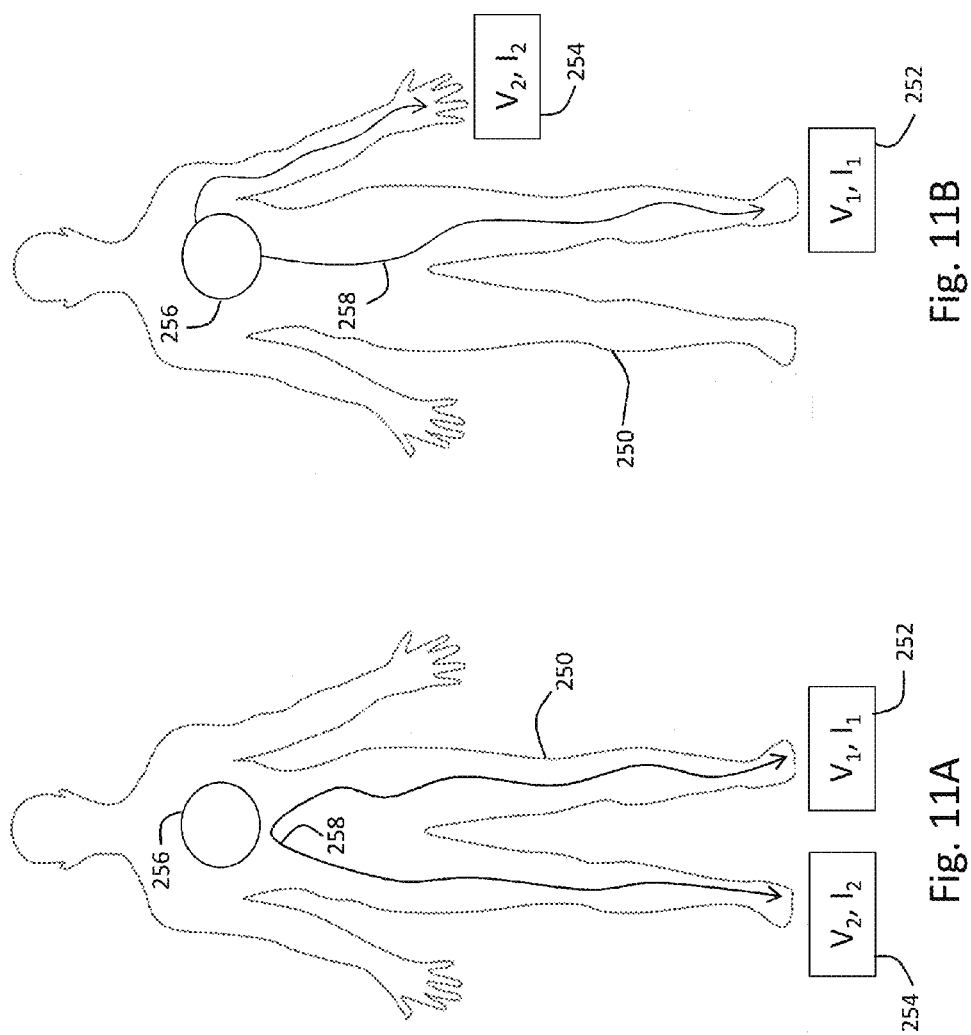

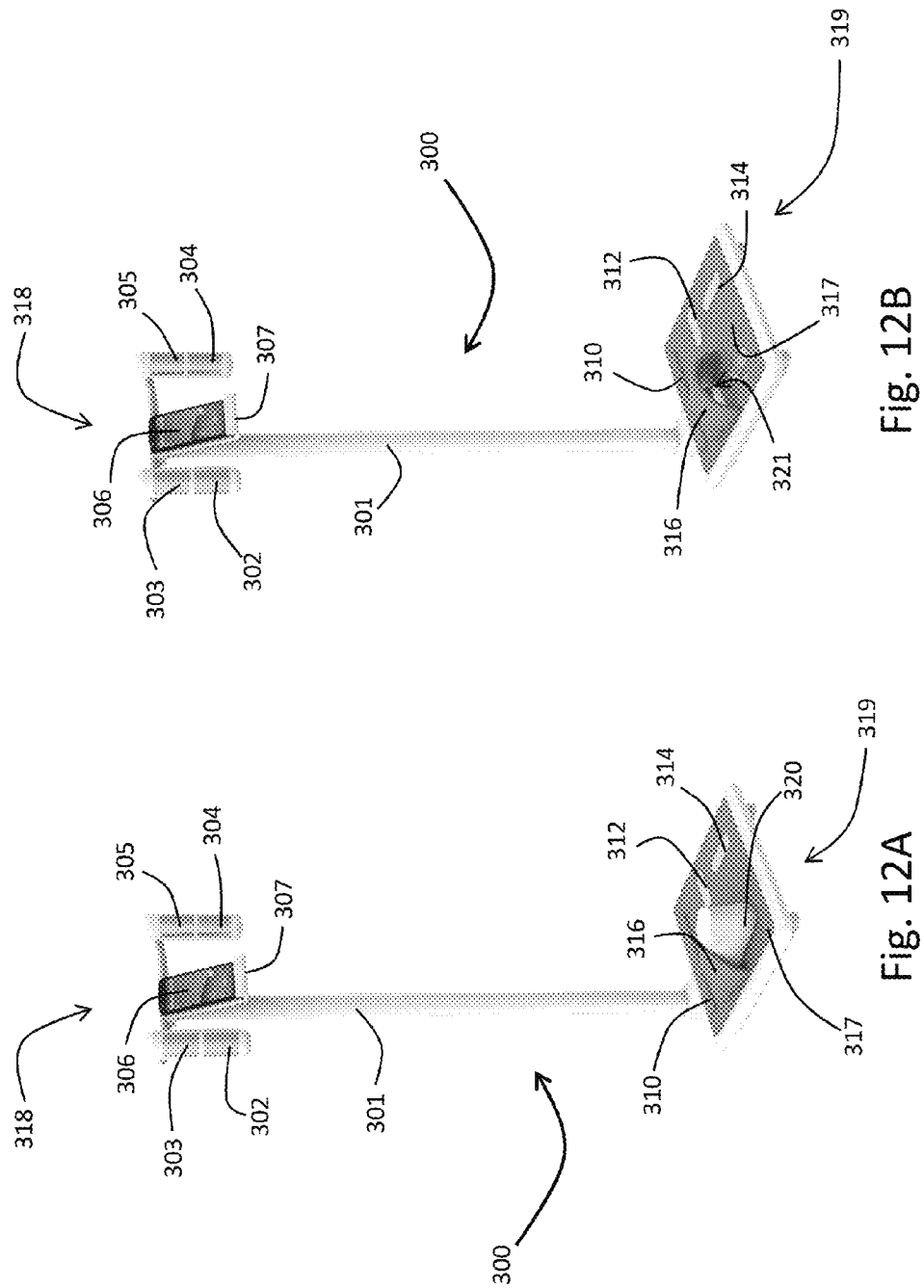

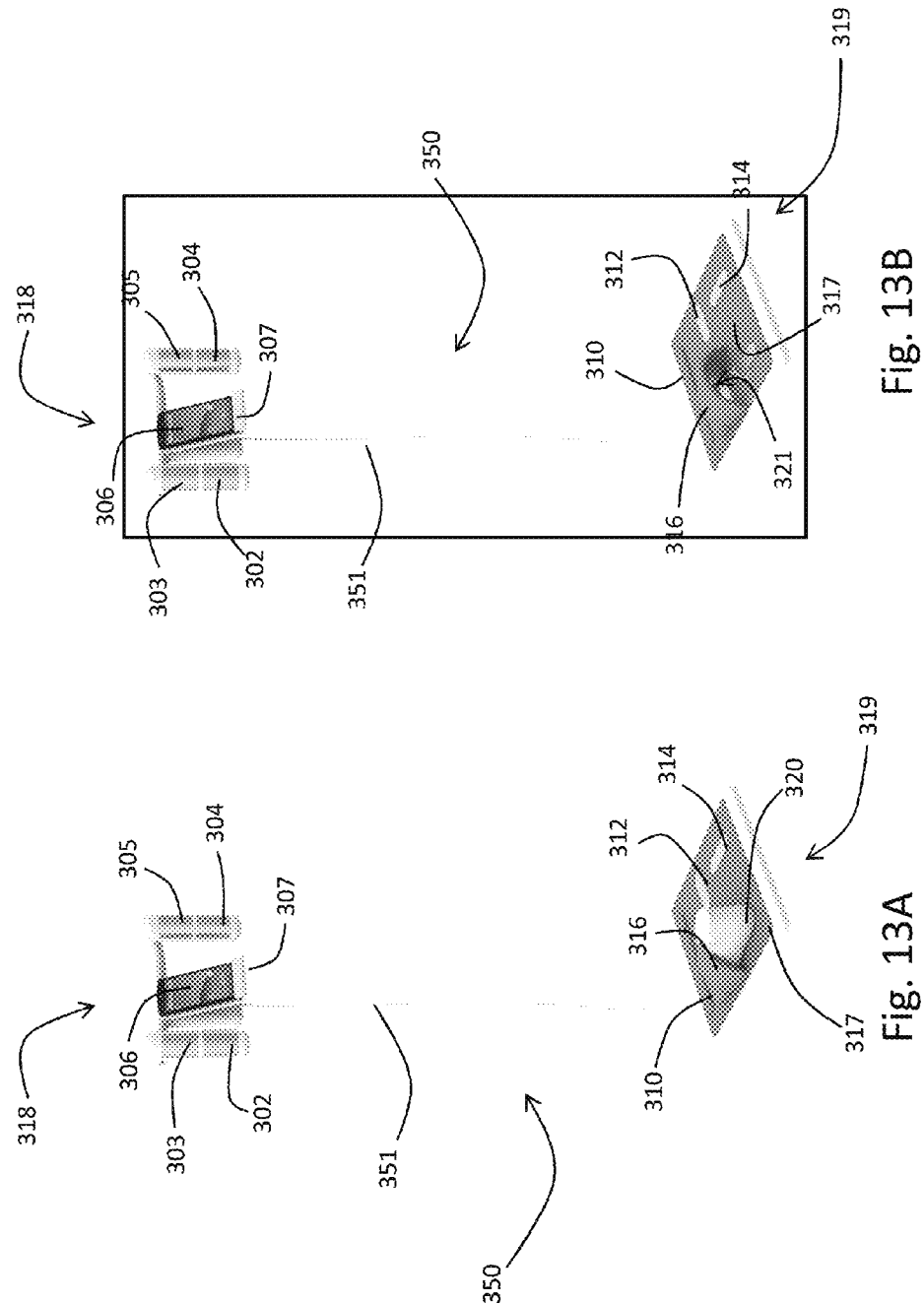

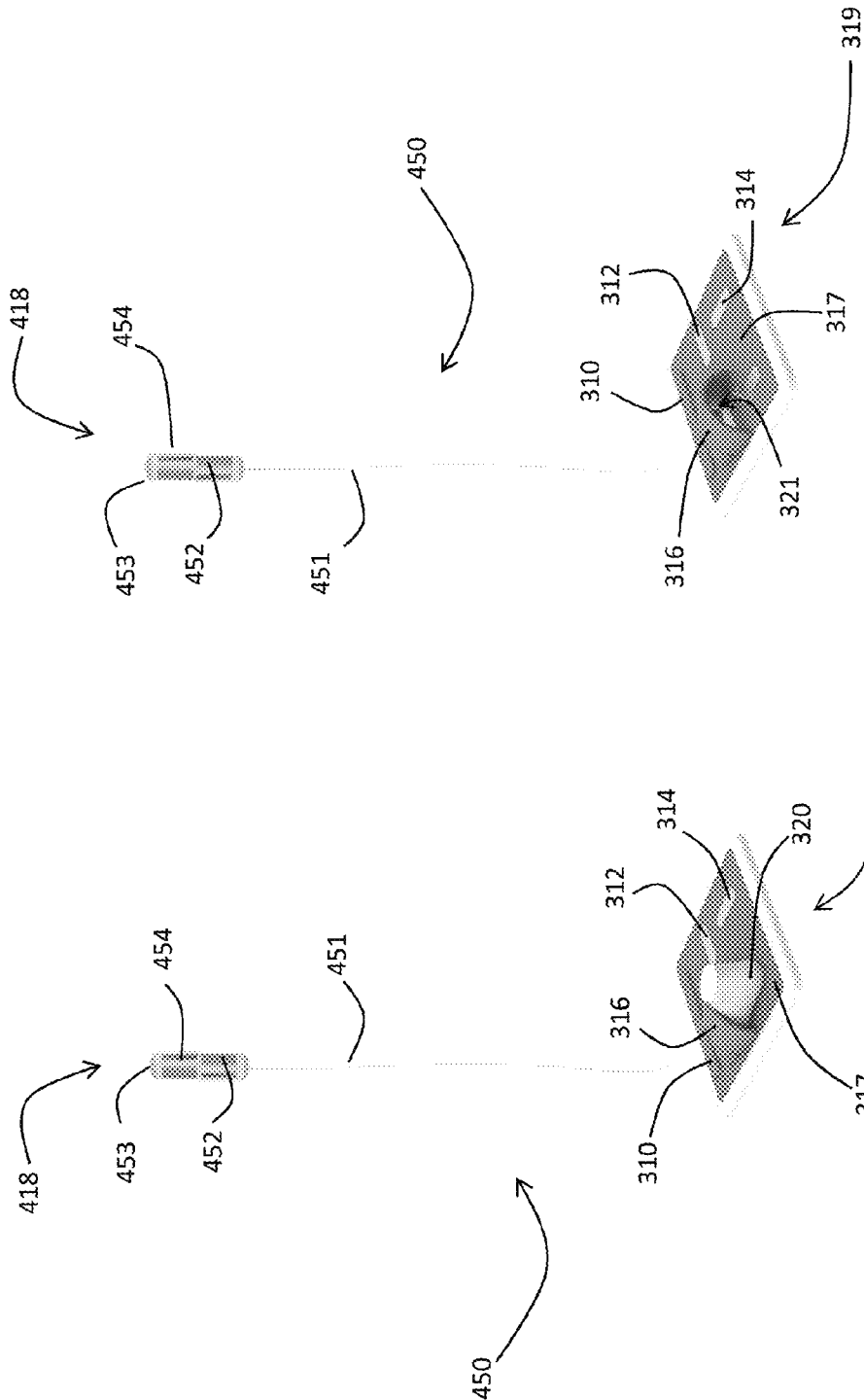

FLOORMAT PHYSIOLOGICAL SENSOR

BACKGROUND AND FIELD OF THE INVENTION

1. Field of the Invention

The invention relates to sensors that measure physiological signals from patients, and the use of such sensors.

2. General Background

Known electrical or digital weight scales typically use a load cell, integrated into a Wheatstone Bridge circuit, to measure a patient's weight. In such devices, the load cell exhibits a small, force-dependent resistance changes when the patient steps on the scale. The Wheatstone Bridge features four resistors, at least one of which is part of the load cell, and a measurable/ascertainable voltage change across Bridge varies with the force applied to the load cell. The voltage change thus correlates to the patient's weight. Once the scale is calibrated, the voltage is digitized and processed and ultimately converted into a weight, which is then displayed to the patient.

More advanced electrical or digital weight scales include stainless steel electrodes and associated circuitry to measure the patient's bioimpedance and/or bioreactance signals. Algorithms process parameters extracted from these signals to estimate parameters such as percent body fat and muscle mass.

Other known sensors measure physiological signals from a patient to determine time-varying waveforms, e.g. thoracic bioimpedance (TBI) and electrocardiogram (ECG) waveforms, with electrodes that attach to the patient's skin. These waveforms can be processed/analyzed to extract other medically relevant parameters such as heart rate (HR), respiration rate (RR), heart rate variability (HRV), stroke volume (SV), cardiac output (CO), and information relating to thoracic fluids, e.g. thoracic fluid index (TFC). Certain physiological conditions can be identified from these parameters using one-time measurements; other conditions require observation of time-dependent trends in the parameters in order to identify the underlying condition. In all cases, it is important to measure the parameters with high repeatability and accuracy.

Some conditions require various physiological parameters to be measured over a relatively short period of time in order to identify the condition. For example, Holter monitors can characterize various types of cardiac arrhythmias by measuring HR, HRV, and ECG waveforms over periods ranging from a day to a few weeks. On the other hand, chronic diseases such as congestive heart failure (CHF) and end-stage renal disease (ESRD) typically require periodic measurements of fluids and weight throughout the patient's life in order to identify the condition. Not surprisingly, patient compliance with measurement routines typically decreases as the measurement period increases. This is particularly true when measurements are made outside of a conventional medical facility, e.g., at the patient's home or in a residential facility such as a nursing home.

Furthermore, the measured values of some physiological parameters will vary with the location at which the parameters are measured, while those associated with other physiological parameters are relatively independent of the location at which the parameters are measured. For example, parameters such as HR, which depends on the time-dependent variation of R-R intervals in ECG waveforms, are relatively insensitive to sensor positioning. Likewise, pulse oximetry (SpO2) and pulse rate (PR), as measured with a pulse oximeter, show little variance with measurement location.

On the other hand, measurements that depend on amplitude-dependent features in waveforms, such as TFC, will be strongly dependent on the measurement location, e.g. the positioning of electrodes. In the case of TFC, for example, the measured value depends strongly on the sensed impedance between a set of electrodes. And this, in turn, will vary with the electrodes' placement. For TFC deviation in the day-to-day placement of the electrodes can result in measurement errors. This, in turn, can lead to misinformation (particularly when trends of the measured parameters are to be extracted), thereby nullifying the value of such measurements and thus negatively impacting treatment.

Like TFC, measured values of blood pressure (e.g. systolic (SYS) and diastolic (DIA) pressure), are typically sensitive to the location at which the parameter is measured. For example, blood pressure measured at the brachial artery with a sphygmomanometer (i.e. a manual blood pressure cuff) or with an oscillomeric device (i.e. an automated blood pressure cuff) will typically be different from that measured at other locations on the body, such as the wrist, thigh, finger, or even the opposite arm. Body temperature (TEMP) is similarly dependent on the location at which it is measured.

3. Sensors, Devices, and Relevant Physiology

Disposable electrodes that measure ECG and TBI waveforms are typically worn on the patient's chest or legs and include: i) a conductive hydrogel that contacts the patient's skin; ii) a Ag/AgCl-coated eyelet that contacts the hydrogel; iii) a conductive metal post that connects to a lead wire or cable extending from the sensing device; and iv) an adhesive backing that adheres the electrode to the patient. Unfortunately, during a measurement, the lead wires can pull on the electrodes if the device is moved relative to the patient's body, or if the patient ambulates and snags the lead wires on surrounding objects. Such pulling can be uncomfortable or even painful, particularly where the electrodes are attached to hirsute parts of the body, and this can inhibit patient compliance with long-term monitoring. Moreover, these actions can degrade or even completely eliminate adhesion of the electrodes to the patient's skin, and in some cases completely destroying the electrodes' ability to sense the physiological signals at various electrode locations.

Some devices that measure ECG and TBI waveforms are worn entirely on the patient's body. These devices have been developed to feature simple, patch-type systems that include both analog and digital electronics connected directly to underlying electrodes. Such devices, like the Holter monitors described above, are typically prescribed for relatively short periods of time, e.g. for a period of time ranging from a day to several weeks. They are typically wireless and include features such as Bluetooth® transceivers to transmit information over a short distance to a second device, which then transmits the information via a cellular radio to a web-based system.

SpO2 values are almost always measured at the patient's fingers, earlobes, or, in some cases, toes. In these cases, patients wear an optical sensor to measure photoplethysmogram (PPG) waveforms, which are then processed to yield SpO2 and PR values. TEMP is typically measured with a thermometer inserted into the patient's mouth.

Assessing TFC, weight, and hydration status is important in the diagnosis and management of many diseases. For example, ESRD occurs when a patient's kidneys are no longer able to work at a level needed for day-to-day life. The disease is most commonly caused by diabetes and high blood pressure, and is characterized by swings in SYS and DIA along with a gradual increase in fluids throughout the body. Patients suffering from ESRD typically require hemodialysis or ultrafiltration to remove excess fluids. Thus, accurate measurement of TFC to identify ESRD can eliminate the need for empirical clinical estimations that often lead to over-removal or under-removal of fluid during dialysis, thereby preventing hemodynamic instability and hypotensive episodes (Anand et al., "*Monitoring Changes in Fluid Status With a Wireless Multisensor Monitor: Results From the Fluid Removal During Adherent Renal Monitoring (FARM) Study*," Congest Heart Fail. 2012; 18:32-36). A similar situation exists with respect to CHF, which is a complicated disease typically monitored using a "constellation" of physiological factors, e.g., fluid status (e.g. TFC), vital signs (i.e., HR, RR, TEMP, SYS, DIA, and SpO2), and hemodynamic parameters (e.g. CO, SV). Accurate measurement of these parameters can aid in managing patients, particularly in connection with dispensing diuretic medications, and thus reduce expensive hospital readmissions (Packer et al., "*Utility of Impedance Cardiography for the Identification of Short-Term Risk of Clinical Decompensation in Stable Patients With Chronic Heart Failure*," J Am Coll Cardiol 2006; 47:2245-52).

CHF is a particular type of heart failure (HF), which is a chronic disease driven by complex pathophysiology. In general terms, HF occurs when SV and CO are insufficient to adequately perfuse the kidneys and lungs. Causes of this disease are well known and typically include coronary heart disease, diabetes, hypertension, obesity, smoking, and valvular heart disease. In systolic HF, ejection fraction (EF) can be diminished (<50%), whereas in diastolic HF this parameter is typically normal (>65%). The common signifying characteristic of both forms of heart failure is time-dependent elevation of the pressure within the left atrium at the end of its contraction cycle, or left ventricular end-diastolic pressure (LVEDP). Chronic elevation of LVEDP causes transudation of fluid from the pulmonary veins into the lungs, resulting in shortness of breath (dyspnea), rapid breathing (tachypnea), and fatigue with exertion due to the mismatch of oxygen delivery and oxygen demand throughout the body. Thus, early compensatory mechanisms for HF that can be detected fairly easily include increased RR and HR.

As CO is compromised, the kidneys respond with decreased filtration capability, thus driving retention of sodium and water and leading to an increase in intravascular volume. As the LVEDP rises, pulmonary venous congestion worsens. Body weight increases incrementally, and fluids may shift into the lower extremities. Medications for HF are designed to interrupt the kidneys' hormonal responses to diminished perfusion, and they also work to help excrete excess sodium and water from the body. However, an extremely delicate balance between these two biological treatment modalities needs to be maintained, since an increase in blood pressure (which relates to afterload) or fluid retention (which relates to preload), or a significant change in heart rate due to a tachyarrhythmia, can lead to decompensated HF. Unfortunately, this condition is often unresponsive to oral medications. In that situation, admission to a hospital is often necessary for intravenous diuretic therapy.

In medical centers, HF is typically detected using Doppler/ultrasound, which measures parameters such as SV, CO, and EF. In the home environment, on the other hand, gradual weight gain measured with a simple weight scale is likely the most common method used to identify CHF. However, by itself, this parameter is typically not sensitive enough to detect the early onset of CHF—a particularly important stage in the condition when the condition may be ameliorated simply and effectively by a simple change in medication or diet.

SV is the mathematical difference between left ventricular end-diastolic volume (EDV) and end-systolic volume (ESV), and represents the volume of blood ejected by the left ventricle with each heartbeat; a typical value is about 70-100 mL. EF relates to EDV and ESV as described below in Equation 1:

$$EF = \frac{SV}{EDV} = \frac{EDV - ESV}{EDV} \qquad (1)$$

CO is the average, time-dependent volume of blood ejected from the left ventricle into the aorta and, informally, indicates how efficiently a patient's heart pumps blood through their arterial tree; a typical value is about 5-7 L/min. CO is the product of HR and SV, i.e., $$CO = SV \times HR \qquad (2)$$

CHF patients—particular those suffering from systolic HF—may receive implanted devices such as pacemakers and/or cardioverter-defibrillators to increase EF and subsequent blood flow throughout the body. These devices may include circuitry and algorithms to measure the electrical impedance between different leads of the device. Some implanted devices process this impedance to calculate a "fluid index". As thoracic fluid increases in the CHF patient, the impedance typically is reduced, and the fluid index increases. Thus, the fluid index, when read by an interrogating device placed outside the patient's body, can indicate the onset of heart failure.

4. Clinical Solutions

Many of the above-mentioned parameters can be used as early markers or indicators that signal the onset of CHF. EF is typically low in patients suffering from this chronic disease, and it can be further diminished by factors such as a change in physiology, an increase in sodium in the patient's diet, or non-compliance with medications. This is manifested by a gradual decrease in SV, CO, and SYS that typically occurs between two and three weeks before hospitalization becomes necessary to treat the condition. The reduction in SV and CO diminishes perfusion to the kidneys. As noted above, these organs then respond with a reduction in their filtering capacity, thus causing the patient to retain sodium and water and leading to an increase in intravascular volume. This, in turn, leads to congestion, which is manifested to some extent by a build-up of fluids in the patient's thoracic cavity (e.g. TFC). Typically, a detectable increase in TFC occurs about 1-2 weeks before hospitalization becomes necessary. Body weight increases after this event (typically by between three and five pounds), thus causing fluids to shift into the lower extremities. At this point, the patient may experience an increase in both HR and RR to increase perfusion. Nausea, dyspnea, and weight gain typically grow more pronounced a few days before hospitalization becomes necessary. As noted above, a characteristic of decompensated HF is that it is often unresponsive to oral medications; thus, at this point, intravenous diuretic therapy in a hospital setting often becomes mandatory. A hospital stay for intravenous diuretic therapy typically lasts about 4 days, after which the patient is discharged and the above-described cycle may start over once again.

Such cyclical pathology and treatment is physically taxing on the patient, and economically taxing on society. In this regard, CHF and ESRD affect, respectively, about 5.3 million and 3 million Americans, resulting in annual healthcare costs estimated at $45 billion for CHF and $35 billion for ESRD. CHF patients account for approximately 43% of annual Medicare expenditures, which is more than the combined expenditures for all types of cancer. Somewhat disconcertingly, roughly $17 billion of this is attributed to hospital readmissions. CHF is also the leading cause of mortality for patients with ESRD, and this demographic costs Medicare nearly $90,000/patient annually. Thus, there understandably exists a profound financial incentive to keep patients suffering from these diseases out of the hospital. Starting in 2012, U.S. hospitals have been penalized for above-normal readmission rates. Currently, the penalty has a cap of 1% of payments, growing to over 3% in the next three years.

Of some promise, however, is the fact that CHF-related hospital readmissions can be reduced when clinicians have access to detailed information that allows them to remotely titrate medications, monitor diet, and promote exercise. In fact, Medicare has estimated that 75% of all patients with ESRD and/or CHF could potentially avoid hospital readmissions if treated by simple, effective programs.

Thus, in order to identify precursors to conditions such as CHF and ESRD, physicians can prescribe physiological monitoring regimens to patients living at home. Typically, such regimens require the use of multiple standard medical devices, e.g. blood pressure cuffs, weight scales, and pulse oximeters. In certain cases, patients use these devices daily and in a sequential manner, i.e., one device at a time. The patient then calls a central call center to relay their measured parameters to the call center. In more advanced systems, the devices are still used in a sequential manner, but they automatically connect through a short-range wireless link (e.g. a Bluetooth® system) to a "hub," which then forwards the information to a call center. Often, the hub features a simple user interface that presents basic questions to the patient, e.g. questions concerning their diet, how they are feeling, and whether or not medications were taken.

Ultimately, however, and regardless of how sophisticated such instrumentation may be, in order for such monitoring to be therapeutically effective, it is important for the patient to use their equipment consistently, both in terms of the duration and manner in which it is used. Less-than-satisfactory consistency with the use of any medical device (in terms of duration and/or methodology) may be particularly likely in an environment such as the patient's home or a nursing home, where direct supervision may be less than optimal.

SUMMARY OF THE INVENTION

In view of the foregoing, it would be beneficial to provide a physiological sensor or monitoring device that is suitable for home use. Particularly valuable would be a monitoring device that conveniently measures a collection of vital signs and hemodynamic parameters, and which fosters patient compliance and regular use. Ideally, the monitoring device is easy to use and features a simple form factor that integrates into the patient's day-to-day activities. A sensor according to the invention, which facilitates monitoring a patient for HF, CHF, ESRD, cardiac arrhythmias, and other diseases, is designed to achieve this goal.

More specifically, the sensor according to this invention is configured generally like a floormat or conventional weight-measuring scale, and therefore is referred to colloquially herein as "the floormat." Using a plurality of sensors, the floormat measures and/or calculates all vital signs along with the sophisticated hemodynamic parameters discussed above in just a few moments (i.e., on the order of two or three minutes).

Preferably the floormat is used daily, and collects information that can be analyzed to determine time-dependent trends. It sends information through a wireless interface, which typically includes the patient's mobile device (e.g. a tablet or smartphone), to a web-based system. The information it collects may be analyzed to detect the early onset of many diseases, e.g. CHF. Ultimately, the floormat can provide clinicians with information that, when acted on, may prevent hospitalization.

More particularly, the floormat measures the following parameters from a patient: HR, PR, SpO2, RR, SYS, DIA, TEMP, a thoracic fluid index (TFI), SV, CO, weight, percent body fat, muscle mass, and parameters sensitive to blood pressure called pulse arrival time (PAT) and vascular transit time (VTT). Collectively, as used herein, PAT and VTT are referred to as pulse transit times (PTTs).

The floormat measures SYS and DIA using a pressure-delivery system that features a bladder similar to a blood pressure cuff. Additionally, using SV, a first algorithm employing a linear model can estimate the patient's pulse pressure (PP). And following this pressure-applying measurement, a second algorithm can process PP, PAT and/or VTT, and a calibration from the pressure-applying measurement to estimate SYS and DIA in a cuffless fashion. Thus the floormat can measure blood pressure using both cuff-based and cuffless techniques. Advantageously, with this configuration, blood pressure values obtained using the direct, pressure-applying mechanism can be used to calibrate the cuffless blood pressure components (hardware and/or software), e.g., every two weeks or so, to keep the accuracy of the floormat optimal. (In other words, the floormat—as an overall, integrated device—is self-calibrating.) In this manner, patients who are averse to having their blood pressure taken using a cuff can minimize their use of the pressure-applying measurement, relying on it occasionally for such calibration purposes while maintaining the floormat's ability to provide accurate, therapeutically meaningful information.

More particularly, as described in greater detail below, the floormat measures the above-described parameters when a patient stands on it for about 2 minutes. To accomplish this, the floormat includes the following sensor subsystems: 1) an ECG system, with two permanent, integrated ECG electrodes that are used to generate an ECG waveform from which HR and HRV are determined; 2) an impedance system, with four permanent, integrated impedance electrodes that are used to generate a bioimpedance (BI) waveform from which TFI, SV, CO, body fat, and muscle mass values are determined; 3) an optical system that generates a collection of PPG waveforms from which SpO2 is determined; 4) a direct or pressure-applying blood pressure system, including an inflatable bladder housing the optical system, that applies a light pressure to the patient's foot and generates a pressure waveform for determining blood pressure; and 5) a scale system that measures the patient's weight along with percent body fat and muscle mass. The ECG and impedance electrodes, which suitably are made from stainless steel or other conductive material, are generally located on the floormat's top surface so as to make contact with the soles of the patient's feet when the patient steps onto the floormat. The system may also have an additional electrode that the patient holds during a measurement, which provides for alternate electrical pathways through the body that can be used to cross-check against the physiological parameter values obtained via foot-to-foot electrical pathways.

A digital processing system featuring a microprocessor, a wireless transmitter, and an analog-to-digital converter processes waveforms measured/generated by the corresponding sensor of each of the various subsystems to determine the associated physiological information described above. A rechargeable battery powers the floormat.

The floormat transmits information to a mobile device, e.g. a cell phone or tablet computer, which can display numerical values, waveforms, graphs, etc. The mobile device, in turn, transmits information to a web-based system, where it can be viewed, e.g., by patients, clinicians, and family members.

More specifically, in one aspect, the invention features a system for measuring a blood pressure value from a patient. The system includes: 1) a base featuring a bottom surface configured to rest on or near a substantially horizontal surface, and a top surface configured to receive at least one of the patient's feet; 2) a pressure-delivery system connected to the top surface and including an opening which covers a portion of at least one of the patient's feet when it is in contact with the top surface, an featuring a flexible member configured to apply pressure to a portion of at least one of the patient's feet and a pressure sensor configured to measure the applied pressure; and 3) a processing system in electrical contact with the pressure sensor, and configured to receive signals from it and convert them into a set of pressure values, and then analyze the set of pressure values to determine the blood pressure value.

The structure, as used herein, is an embodiment of the floormat.

In another aspect, the system also includes a weight-measuring system connected to the structure's top surface and featuring an electrical system that measures a set of voltages that correlates with a force applied to the top surface.

In embodiments, the flexible member is a bladder (that can be filled, e.g., with a fluid such as air), and the pressure-delivery system includes a pump. The pump connects to the bladder and, in embodiments, a valve, and is configured to pump air into the bladder when the pump is powered on. The pressure sensor connects to the bladder and is configured to measure a pressure within the bladder. In embodiments, the bladder is formed as a strap that receives air from the pump, with a first distal end of the strap connected to the top surface, and a second distal end of the strap connected to the top surface.

Typically the processing system features computer code that analyzes the set of pressure values to determine the blood pressure value. The computer code can run on, e.g., a microcontroller or microprocessor. For example, the pressure values can be a set of pressure-dependent oscillations that depend on the patient's blood pressure, and the computer code can analyze these to determine a blood pressure value. Typically, each pressure-dependent oscillation in the set of pressure-dependent oscillations is characterized by a pressure and amplitude value, and the computer code is further configured to determine the pressure-dependent oscillation having a maximum amplitude value. From this the system calculates the MAP. In related embodiments, the computer code is further configured to determine SYS from a first pressure-dependent oscillation characterized by an amplitude that, when divided by the maximum amplitude of the pressure-dependent oscillations, is substantially equivalent to a first pre-determined ratio (typically between 0.4-0.8, and most preferably about 0.6). In yet another related embodiment, the computer code is further configured to determine DIA from a second pressure-dependent oscillation characterized by an amplitude that, when divided by the maximum amplitude of the pressure-dependent oscillations, is substantially equivalent to a second pre-determined ratio (typically between 0.4-0.8, and most preferably about 0.7).

In embodiments, the set of pressure-dependent oscillations are measured while the pressure-delivery system inflates or deflates the flexible member.

In other embodiments, the electrical system within the weight-measuring system features a Wheatstone Bridge that connects electrically with an amplifier system. Here, the system's processing system is further configured to receive the set of voltages, and analyze them to determine a value of weight corresponding to the force applied on the top surface.

In another aspect, the invention features a system for measuring a stroke volume value from a patient. The system features: 1) a mechanical structure similar to that described above; 2) an electrical impedance system connected to the structure's top surface and including at least four electrodes, at least one of which is configured to inject an electrical current into the patient's feet, and at least one of which is configured to measure a signal induced by the electrical current and representative of an impedance plethysmogram; and 3) a processing system in electrical contact with the electrical impedance system, and configured to receive signals from it and convert them into a set of impedance values which it then analyzes to determine the stroke volume value.

In embodiments, the system for measuring a stroke volume value features a weight-measuring system similar to that described above.

In other embodiment, the electrical impedance system features an electrical system that injects a current modulated at a frequency between 25-125 kHz (and preferably about 100 kHz). Typically the electrical impedance system features two electrodes that inject the electrical current that are disposed on the structure's top surface, with one electrode located substantially on the left-hand side of the top surface and configured to inject electrical current into the patient's left foot, and one electrode located substantially on the right-hand side of the top surface and configured to inject electrical current into the patient's right foot. It also typically includes two additional electrodes, each configured to measure a signal induced by the electrical current, wherein both electrodes are connected to the top surface, and one electrode is located substantially on the left-hand side of the top surface and configured to measure a signal from the patient's left foot, and one electrode is located substantially on the right-hand side of the top surface and configured to measure a signal from the patient's right foot. In other embodiments, the system also includes a hand-held component with at least two electrodes similar to those described above.

In embodiments, the processing system features computer code configured to analyze the set of impedance values to determine the stroke volume value. For example, the computer code can calculate a derivative of the set of impedance values to determine a dΔZ(t)/dt waveform, from which it calculates a maximum value or an area of a pulse therein. The computer code can also analyze the dΔZ(t)/dt waveform to determine an ejection time or a baseline impedance ($Z_o$) value. The computer code can then process these values to determine SV using the equation:

$$SV \sim \frac{(d\Delta Z(t)/dt)_{max}}{Z_o} \times LVET \quad (3)$$

or, alternatively, the equation:

$$SV \sim \sqrt{\frac{(d\Delta Z(t)/dt)_{max}}{Z_o}} \times LVET \qquad (4)$$

In embodiments, the system's weight-measuring system measures a set of voltages that correlates with a force applied to the top surface, and from these calculate the user's weight. The processing system can then use the weight to determine SV from the equation:

$$SV = V_c \times \frac{(d\Delta Z(t)/dt)_{max}}{Z_o} \times LVET \qquad (5)$$

or, alternatively, the equation:

$$SV = V_c \times \sqrt{\frac{(d\Delta Z(t)/dt)_{max}}{Z_o}} \times LVET \qquad (6)$$

where $V_c$ is a volume conductor calculated from the value of weight.

In still other aspects, the system calculates CO by also measuring HR as described below (e.g. using an ECG waveform), and then collectively processing SV and HR (e.g., by taking the product) to determine CO.

In another aspect, the invention provides a system for measuring an SpO2 value from a patient. The system features: 1) a mechanical structure similar to that described above; 2) an optical system connected to the structure's top surface and featuring a first light source that emits infrared radiation, a second light source that emits red radiation, and a photodetector configured to receive infrared and red radiation after it irradiates at least one of the patient's feet to generate, respectively, a first and second set of signals; and 3) a processing system in electrical contact with the optical system, and configured to receive the first and second set of signals from the optical system and convert them into, respectively, a first and second set of values that it then analyzes to determine the SpO2.

In embodiments, the system for measuring an SpO2 value features a weight-measuring system similar to that described above.

In embodiments, the first light source is configured to emit optical radiation between 880 and 920 nm (preferably about 905 nm) and the second light source is configured to emit optical radiation between 640 and 680 nm (preferably about 660 nm). Typically the first and second light sources and the photodetector are connected directly to the structure's top surface, and the photodetector is configured to receive infrared and red radiation after it reflects off one of the patient's feet. Alternatively, the first and second light sources are connected to a member that, in turn, connects directly to the structure's top surface, and the member is configured to cover at least a portion of one of the patient's feet. For example, the member can be a flexible strap connected at its distal ends to the top surface. In this case, the photodetector is connected directly to the structure's top surface, and is configured to receive infrared and red radiation after it transmits through the patient's feet.

In embodiments, the processing system features computer code configured to analyze the first set of values to determine an AC component (infrared(AC)) and a DC component (infrared(DC)), and the second set of values to determine an AC component (red(AC)) and a DC component (red(DC)). It then processes these components to determine the SpO2 value. Processing, for example, may use the following equation to determine a ratio of ratios (RoR):

$$RoR = \frac{red(AC)/red(DC)}{infrared(AC)/infrared(DC)} \qquad (7)$$

and then determine the RoR according to the following equation to determine the SpO2 value:

$$SpO2\ value = (a + b \times RoR + c \times RoR) \times 100 \qquad (8)$$

wherein a, b, and c are pre-determined constants.

In another aspect, the invention provides a system for measuring an RR value from a patient. The system features: 1) a mechanical structure similar to that described above; 2) an electrical impedance system similar to that described above and connected to the structure's top surface and configured to measure an impedance plethysmogram; and 3) a processing system in electrical contact with the electrical impedance system, and configured to receive signals from it and convert them into a set of impedance values that it then analyzes to determine the RR value.

In embodiments, the system for measuring an RR value features a weight-measuring system similar to that described above.

In embodiments, the electrical impedance system is similar to the four-electrode system described above, and may include the hand-held component. Here, the processing system includes computer code configured to analyze the set of impedance values to determine the RR value. During use, for example, the electrical system generates impedance values that include oscillations, and the processing system's computer code analyzes oscillations to determine the RR value. Alternatively, the set of impedance values feature time-dependent pulsations, and the processing system's computer code analyzes a separation in neighboring pulsations to determine the RR value. Or the computer code can determine a mathematical derivative of the set of impedance values, and then process this to determine the RR value.

In another aspect, the invention provides a system for measuring a PTT value from a patient. The system features: 1) a mechanical structure similar to that described above; 2) an electrical impedance system similar to that described above that generates a first set of signals representative of an impedance plethysmogram; 3) a heart rate monitoring system connected to the mechanical structure and featuring a differential amplifier configured to measure a second set of signals representative of a cardiac rhythm from the patient; and 4) a processing system in electrical contact with the electrical impedance system and the heart rate monitoring system, and configured to: i) receive the first signals from the electrical impedance system and convert them into a set of impedance values; ii) analyze the set of impedance values to determine a first time value indicating a first pulsatile component; iii) receive the second set of signals from the heart rate monitoring system and convert them into a set of cardiac rhythm values; iv) analyze the set of cardiac rhythm values to determine a second pulsatile component; and v) collectively process the first and second pulsatile components to determine the PTT value.

In embodiments, the system for measuring a PTT value features a weight-measuring system similar to that described above.

In embodiments, the processing system features computer code configured to: i) calculate a mathematical derivative of the impedance values to determine a set of derivative values; and ii) determine a local maximum of the set of derivative values to determine the first pulsatile component; and/or iii) determine a zero-point crossing of the set of derivative values to determine the first pulsatile component. The computer code may also be configured to: i) estimate the set of derivative values with a mathematical function; and ii) analyze the mathematical function to determine the first pulsatile component.

In embodiments, the computer code is configured to determine a local maximum of the cardiac rhythm values to determine the second pulsatile component, and the cardiac rhythm values are representative of an ECG waveform. For example, the computer code can be configured to determine a QRS complex (e.g. calculate the Q or R point) in the ECG waveform to determine the second pulsatile component. It can also further process the cardiac rhythm values to determine a heart rate value, e.g. by calculating a time interval separating the first and second R points.

In a related aspect, the invention provides a system for measuring a PTT value from a patient that is similar to that described above, but includes an optical system for measuring a photoplethysmogram from the patient. This system may be used in place or in addition to the impedance system. The processing system analyzes photoplethysmogram to determine a pulsatile component, which it then processes to determine the PTT value. In general, the system may use any combination of pulsatile components measured from cardiac rhythm waveforms (e.g., ECG waveforms), impedance plethysmogram waveforms, and photoplethysmogram waveforms to determine a PTT value. In embodiments, each system may also include a weight-measuring system.

In another aspect, the invention features a system for measuring a patient's blood pressure value using PTT, which is measured with the electrical and mechanical structure described above. The system also includes a pressure-delivery system connected to the structure that includes an opening that covers a portion of one of the patient's feet when it is in contact with the structure's top surface. The pressure-delivery system features a flexible member (e.g. a bladder or foot cuff connected to a pump and valve) configured to apply pressure to a portion of the patient's foot, and a pressure sensor configured to measure a first set of signals representative of the applied pressure. The system also includes an optical system connected to the structure that includes a light source that emits optical radiation, and a photodetector that receives the optical radiation after it irradiates a portion of the patient's feet to generate a second set of signals representative of a photoplethysmogram from the patient. A processing system in electrical contact with the pressure sensor and optical system is configured to: 1) receive the first set of signals from the pressure-delivery system and convert them into a set of pressure values; 2) receive the second set of signals from the optical system and convert them into a set of pulsatile signals; and 3) collectively analyze the set of pressure values and the set of pulsatile signals to determine the blood pressure value.

In embodiments, the bladder is formed as a strap, with first and second distal ends of the strap connected to the structure's top surface so that they form an opening that receives air from the pump and/or valve. Computer code in the processing system controls both the pressure-delivery system and the optical system so that the second set of signals representative of a photoplethysmogram are generated while the pressure-delivery system applies pressure to the patient's foot. The code then analyzes the amplitude and a pressure corresponding to at least one of the pulsatile signals, ultimately generating a set of amplitudes corresponding to the set of pulsatile signals, with each corresponding to a unique pressure value. To determine blood pressure, the computer code can then determine an amplitude in the set of amplitudes having a minimum value, and from this estimate SYS. In a related embodiment, the computer code approximates amplitude values in the set of amplitudes with a mathematical function, can then estimates SYS from a minimum value or zero-point crossing of the mathematical function. The computer code can also determine an amplitude having a maximum value from the set of amplitudes (or a mathematical function approximating the set of amplitudes), and from this estimate MAP.

As with the other systems described above, the system for measuring a blood pressure value can also feature a weight-measuring system similar to that described above.

In yet another aspect, the invention provides a system for measuring a fluid value from a patient. The system features a mechanical structure and weight-measuring system similar to those described above. To estimate a patient's fluid value, the system includes an electrical impedance system, similar to that described above, featuring at least four electrodes. The electrical impedance system measures a set of signals representative of an impedance plethysmogram. A processing system in electrical contact with the electrical impedance system processes the signals to determine the fluid value. The electrical impedance system can measure all the signals from the user's feet, or alternatively may include a hand-held component that features at least two electrodes (one to inject current, the other to measure a signal induced by the injected current) to contribute to the measurement. The processing system features computer code that, during a measurement, analyzes the set of impedance values to determine the fluid value. For example, the computer code can calculate an average of the set of impedance values to determine the fluid value.

In addition to providing stand-alone measurements, the floormat may link with other devices through its wireless connection to share information with the other device in either one or two directions. For example, the floormat may measure weight, as described above, and then transmit this information to an external sensor which, in turn, may use this value for a separate calculation. An example of a device that links to the floormat through such a mechanism is the necklace-shaped sensor described in the following patent applications, the contents of which are incorporated herein by reference: "NECK-WORN PHYSIOLOGICAL MONITOR," U.S. Ser. No. 62/049,279, filed Sep. 11, 2014; "NECKLACE-SHAPED PHYSIOLOGICAL MONITOR," U.S. Ser. No. 14/184,616, filed Aug. 21, 2014; and "BODY-WORN SENSOR FOR CHARACTERIZING PATIENTS WITH HEART FAILURE," U.S. Ser. No. 14/145,253, filed Jul. 3, 2014. In such an arrangement or configuration, the necklace-shaped sensor uses the floormat-measured weight value to calibrate its measurement of SV, since one of the factors in the equation for SV ($\delta$) is a function of weight. In a similar arrangement or configuration, the floormat measures blood pressure values (e.g. SYS, DIA, and/or MAP) and transmits these values to the necklace-shaped sensor, which then uses them to calibrate its cuffless measurement of blood pressure. In such cases, for example, the floormat and necklace-shaped sensor suitably communicate through a wireless technology such as Bluetooth® protocols.

The floormat described herein has many advantages. In general, it provides a single, easy-to-use device that a patient can simply step on to measure all their vital signs, complex hemodynamic parameters, and basic wellness-related parameters such as weight, percent body fat, and muscle mass. Such ease of use may increase compliance, thereby motivating patients to use it every day. And with daily use, the floormat, mobile device, and/or cloud-based system can calculate trends in a patient's physiological parameters, thereby allowing better detection of certain disease states and/or management of chronic conditions such as CHF, diabetes, hypertension, COPD, kidney failure, and/or obesity.

Because of its form-factor/configuration and associated modality of use (i.e., simply stepping onto and standing on it), the floormat helps ensure consistent measurement of the various parameters through the patient's feet when used on a daily basis, thereby improving the repeatability and reproducibility of its measurements. This is particularly true given the general similarity of the floormat to a conventional bathroom scale—something most people are used to using on a weekly or even daily basis to determine their health (i.e., weight) status.

Further still, some people—e.g., obese or morbidly obese individuals, for whom various physiological measurements are crucial—can have difficulty using more conventional sensors. That can be due to those patients' size and/or lack of body surfaces that are smooth or "regular" enough to attach electrodes to. Therefore, configuring a physiological sensor so that the patient simply needs to stand on it (perhaps with assistance) for accurate measurements to be taken can advantageously obviate such issues.

Furthermore, data from the floormat can be combined with data from other devices, e.g. wearable devices or other devices within the home, to better characterize a patient. For example, one-time measurements from the floormat (e.g. resting HR, SV, CO, and/or SYS, DIA, and MAP) can be combined with continuous measurements from the wearable device (e.g., continuously measured HR and activity levels) to track a patient's fitness level or progression of a specific disease state. Likewise, data from the floormat can be combined with video or still images from cameras within the patient's home to monitor a patient by collectively processing physiological information along with that indicating their at-home activities (e.g., how much they are eating, sleeping, watching television, etc.). Such information, for example, may indicate the onset of a physiological condition that may require a medical event, e.g. hospitalization.

Still other advantages should be apparent from the following detailed description and from the claims.

BRIEF DESCRIPTION OF THE DRAWINGS

FIG. 4A is a front perspective view of the floormat shown in FIG. 1;

FIG. 4B is a schematic section view of FIG. 4A along sight line 4B;

FIG. 4C is a schematic section view of FIG. 4A along sight line 4C;

FIG. 6A is a rear perspective view of the floormat shown in FIG. 1;

FIG. 6B is a schematic circuit diagram illustrating a blood pressure system from the floormat of FIG. 6A;

FIG. 6C is a schematic circuit diagram illustrating an optical system from the floormat of FIG. 6A;

FIG. 8A is a rear perspective view of the floormat shown in FIG. 1;

FIG. 8B is a schematic circuit diagram from the floormat of FIG. 8A for generating and processing ECG waveforms;

FIG. 8C is a schematic circuit diagram from the floormat of FIG. 8A for generating and processing BI waveforms;

FIG. 9 is a set of time-dependent graphs showing (from top to bottom) ECG, BI, PPG, d(BI)/dt, and d(PPG)/dt waveforms;

FIG. 10A is a front perspective view of the floormat shown in FIG. 1;

FIG. 10B is a schematic section view along the sight line 10B in FIG. 10A;

FIG. 10C is a schematic representation of the weight-measuring load cell shown in FIG. 10B;

FIG. 10D is a schematic circuit diagram illustrating the Wheatstone Bridge used in connection with the load cell of FIG. 10C to measure patient weight;

FIG. 11A is a schematic diagram illustrating current-flow pathways for a first configuration of a floormat according to the invention;

FIG. 11B is a schematic diagram illustrating current-flow pathways for a second configuration of a floormat according to the invention;

FIG. 12A is a perspective view showing an embodiment of the invention featuring a floormat and vertical pole that supports hand-held electrodes and a mobile device;

FIG. 12B is a perspective view showing another alternate embodiment of the invention featuring a floormat and vertical pole that supports hand-held electrodes and a mobile device;

FIG. 13A is a perspective view showing an embodiment of the invention featuring a floormat and flexible cable that supports hand-held electrodes and a mobile device;

FIG. 13B is a perspective view showing yet another an embodiment of the invention featuring a floormat and flexible cable that supports hand-held electrodes and a mobile device;

FIG. 14A is perspective view showing an alternate embodiment of the invention featuring a floormat and flexible cable that supports hand-held electrodes;

FIG. 14B is perspective view showing yet another alternate embodiment of the invention featuring a floormat and flexible cable that supports hand-held electrodes.

DETAILED DESCRIPTION

1. Product Overview

Figure 1:
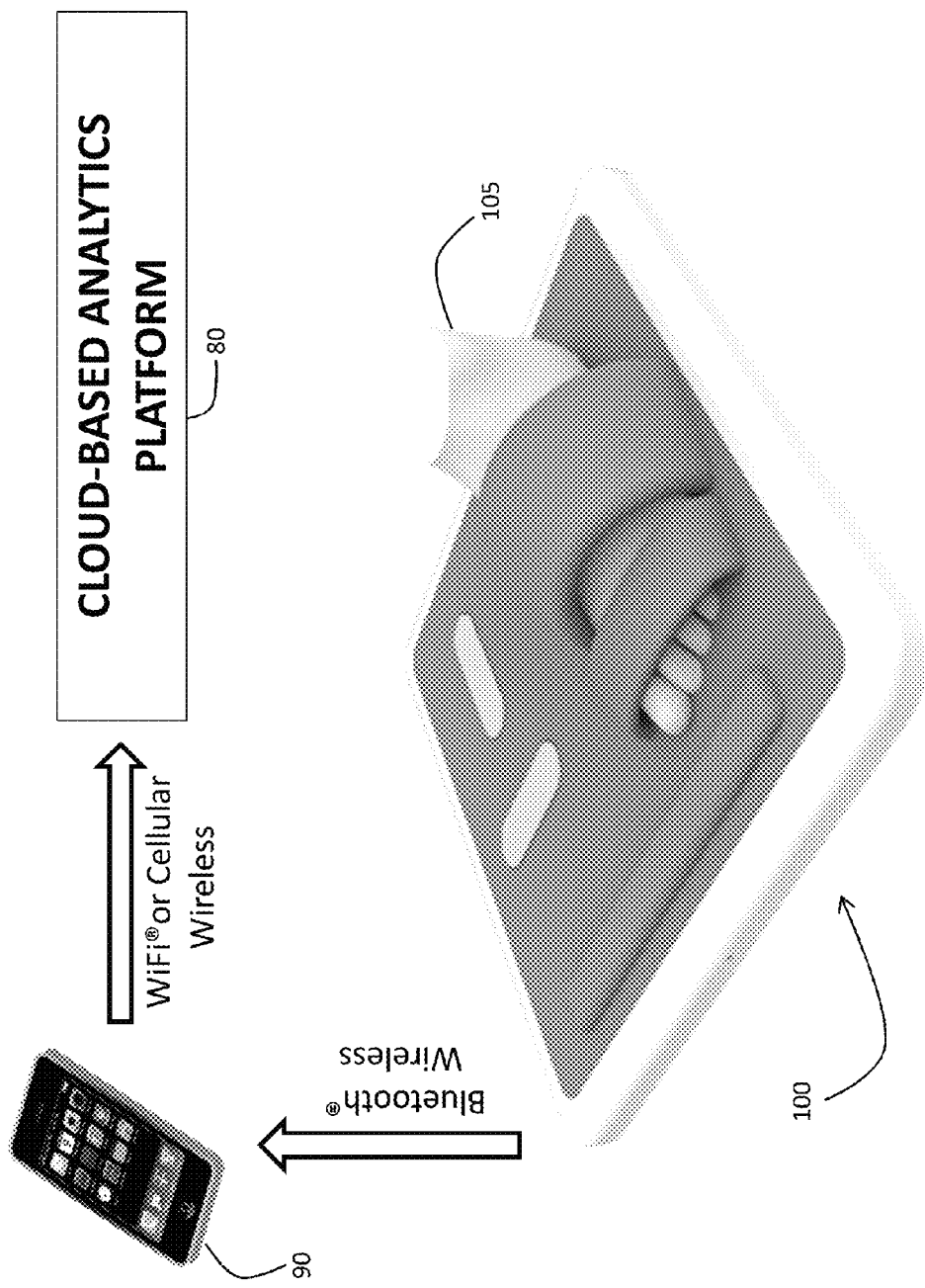
FIG. 1 is a front perspective view of a floormat according to the invention schematically illustrating its use in monitoring a patient.

As shown in FIG. 1, the invention provides a stand-on sensor ("floormat") 100 that measures a number of physiological parameters, e.g. vital signs (e.g. HR, RR, SpO2, SYS, DIA), hemodynamic parameters (CO, SV, TFI), and biometric parameters (weight, percent body fat, muscle mass) of a patient 105. More specifically, the floormat 100 measures these parameters from the patient's feet, as is described in more detail below. In this way, a comprehensive set of physiological data can be measured easily and on a daily basis while the patient 105 simply stands on the floormat 100, in a manner that is similar to how the patient would use a standard bathroom scale to weigh himself or herself.

Once the physiological information is obtained, the floormat 100 wirelessly transmits it, e.g., using a short-range wireless technology (suitably Bluetooth® wireless technology) to a mobile device 90, e.g., a conventional smartphone or tablet computer belonging to the patient. In some embodiments, the floormat 100 may lack any display to render a graphical user interface (GUI) and may rely instead strictly on the mobile device 90 for this functionality, which somewhat simplifies overall construction of the floormat. For example, the GUI could be rendered on the mobile device 90 with a downloadable software application that operates on standard mobile operating systems, e.g., Android or iOS operating systems. During use, the GUI can prompt the patient 105 to step on the floormat 100; display the various information that it measures; plot trends in numerical values; graph time-dependent waveforms; provide other content related to the floormat-measured information; and provide content/information on how to improve the patient's health. It should be appreciated, however, that embodiments of a floormat that do include some form of display are, of course, deemed to be within the scope of the invention.

After the mobile device 90 receives information from the floormat 100, it transmits the information using a long-range wireless technology—suitably based on 802.11b/g/n, i.e. WiFi®, or cellular systems such as those provided by ATT, Cingular, TMobile, etc.—to a cloud-based analytics platform 80. This can be, for example, a software system associated with, e.g., an Internet browser, electronic medical record (EMR), database, and/or website. The cloud-based analytics platform 80 suitably features GUIs for both the patient and clinicians. Suitably, the patient GUI renders only the patient's information, whereas the clinician's GUI renders information collected from a group of patients. Like the GUI on the mobile device 90, the cloud-based analytics platform GUI renders the information; plots trends in specific parameters; and, in general, allows a remote clinician to monitor the patient 105 in their home environment.

Figure 2:
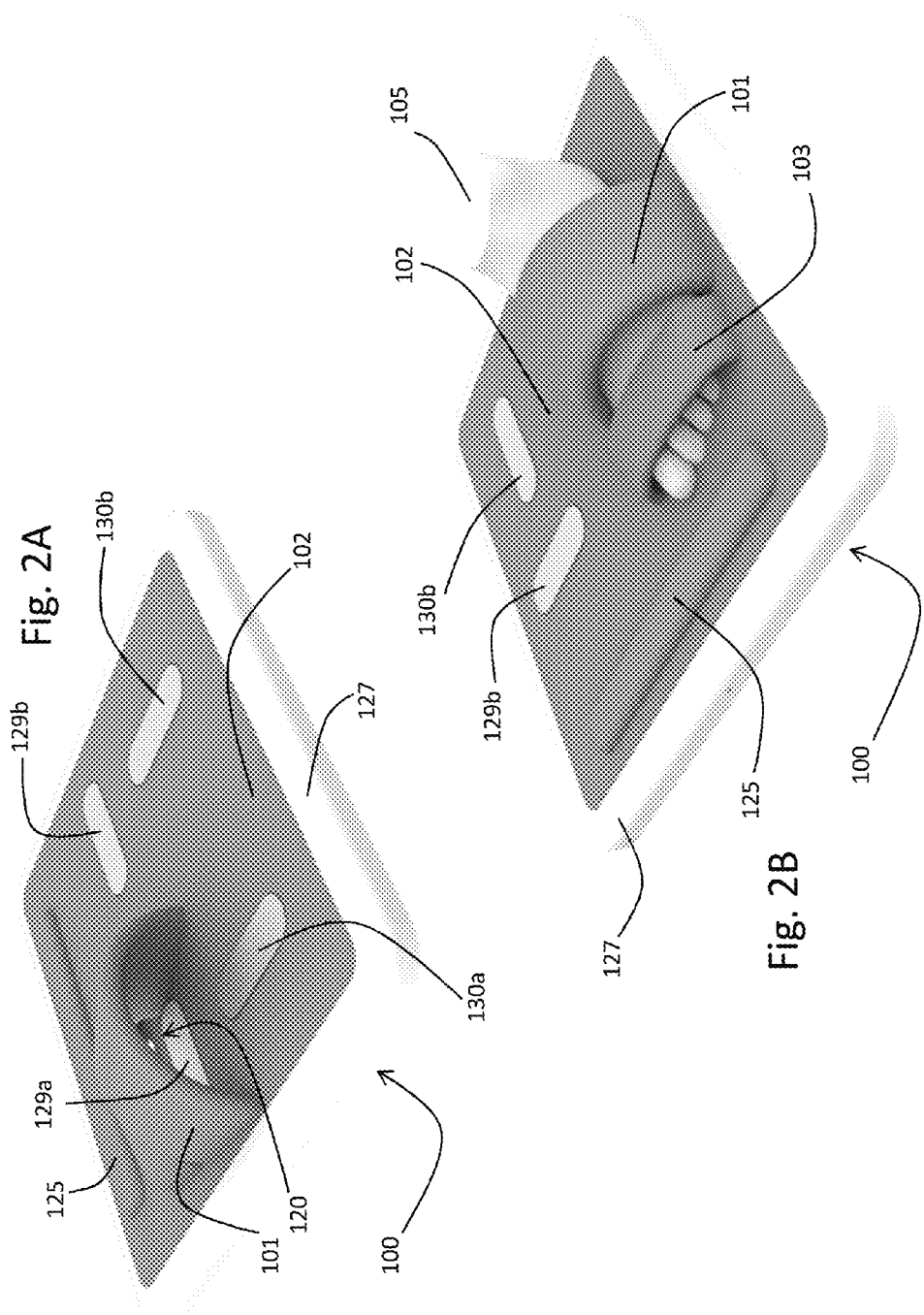
FIG. 2A is a rear perspective view of the floormat shown in FIG. 1.
FIG. 2B is a front perspective view of the floormat shown in FIG. 1.
Figure 3:
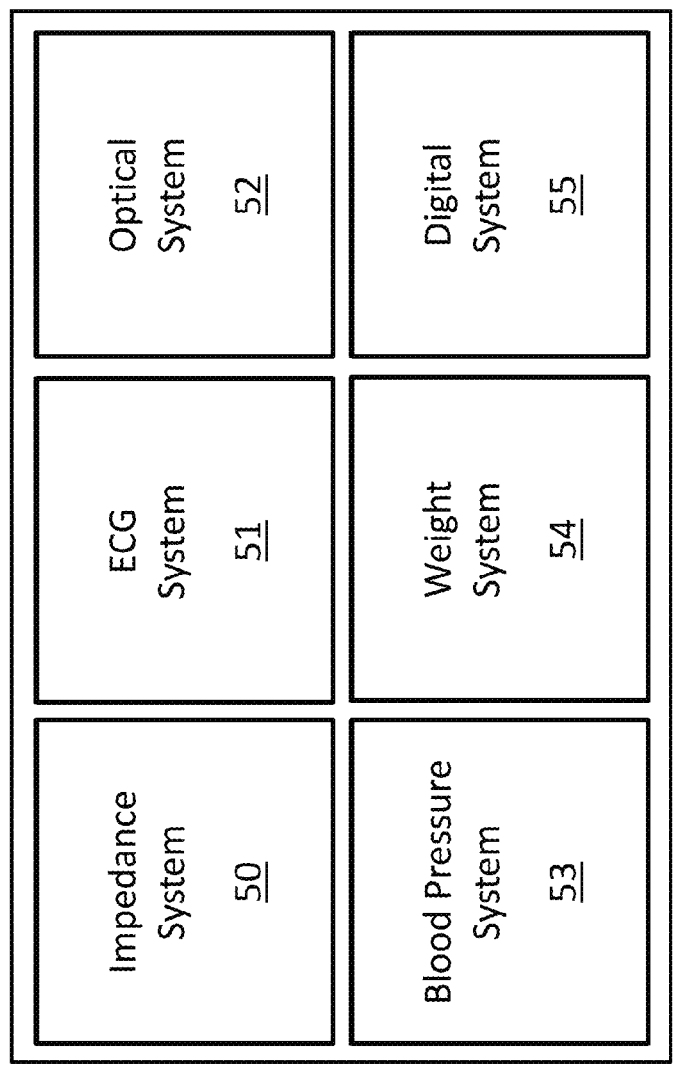
FIG. 3 is a schematic diagram illustrating various sensor subsystems included in the floormat shown in FIG. 1.

As illustrated in FIGS. 2A, 2B, and 3, the floormat 100 includes the following features or subsystems for characterizing the patient: i) an impedance system 50; ii) an ECG system 51; iii) an optical system 52; iv) a blood pressure system 53; v) a weight system 54; and vi) a digital processing system 55. Together, these systems measure and process the above-described physiological information and send it to the mobile device and cloud-based analytics platform for further analysis. These systems 50-55 are integrated within the floormat 100, which provides a simple, easy-to-use device that resembles a conventional weight-measuring scale.

More particularly, the blood pressure system 53 includes back and front straps 101, 103 that form a pocket to receive, for example, the patient's left foot. In other embodiments, however, the straps could be positioned to form a pocket to receive the patient's right foot instead. The straps 101, 103 resemble those present in conventional sandals or bathroom slippers. The back strap 101 includes an inflatable air bladder, described in more detail below, which is coupled to a pressure-delivery system 115. During a measurement, the air bladder and hence the strap 101 inflates and gently constricts blood flow in the patient's foot.

An optical system 120 is housed within or mounted to the front strap 103 in position to face the upper surface of the patient's foot when the patient places his or her foot into the pocket formed by the straps. The optical system 120 measures blood flow and corresponding PPG waveforms from the left foot while pressure is being applied to it, and in this way provides inputs that are used in the blood pressure analysis, as is described in more detail below.

An upper, top layer of material 102, which is suitably composed of silicone rubber, provides a soft, comfortable, non-slip surface for the patient to stand on. The soft, silicone top layer 102 extends over most of the top surface of the floormat 100 and supports the patient's left 105a and right 105b feet during a measurement. Rigid side panels 127, which may be part of a surrounding framework that forms a base for the floormat 100, surround the top surface 102 and help stabilize the floormat 100 when the patient 105 stands on it. The base, of course, should be strong enough to support the weight of an adult patient, e.g., someone weighing up to 350 pounds (or more, perhaps, for use in more clinical healthcare facilities such as obesity-treatment centers). Four support posts (two of which 104a, 104b are shown in the figure) extend from a bottom surface 106 of the floormat, allowing the floormat 100 to rest on a horizontal surface, e.g. a floor. Suitably, the support posts are individually adjustable, e.g., by screwing or unscrewing them into or out of the bottom surface 106 of the floormat 100, so as to level the floormat 100.

A conventional weight-measurement system that uses a Wheatstone Bridge, illustrated and described below in connection with FIG. 10, is located beneath the top layer 102. The weight-measurement system measures signal inputs from strain gauges within the floormat, described in more detail below, to determine the patient's weight.

Four conductive stainless steel electrodes 129a, 129b, 130a, 130b are partially embedded within the top layer of material 102, with upper surfaces of the electrodes exposed so as to make contact with the soles of the patient's feet when the patient stands on the floormat. The electrodes are used to measure electrical signals from the patient's left and right feet simultaneously, which signals are amplified and filtered by circuits on the circuit board 117 to generate BI and ECG waveforms as well as bioreactance impedance signals, the latter of which are used to determine percent body fat and muscle mass. (BI is an impedance waveform that is analogous to TBI, except it is not obtained exclusively from the patient's chest, and therefore does not reference the thorax via a "T" in its acronym.) While stainless steel is a preferred material for the electrodes, other materials may also be used. These include conductive rubber, conductive fabrics, metals other than stainless steel, and materials coated with conductive materials, such as films of Ag/AgCl.

An electronics module 125, which may be housed within a forward portion of the top layer 102, includes all of the electronics for the impedance 50, ECG 51, optical 52, blood pressure 53, weight 54, and digital 55 systems. These systems generally include a number of analog amplifiers and filters, which are described in detail in the following co-pending patent applications entitled "NECK-WORN PHYSIOLOGICAL MONITOR," U.S. Ser. No. 62/049,279, filed Sep. 11, 2014; "NECKLACE-SHAPED PHYSIOLOGICAL MONITOR," U.S. Ser. No. 14/184,616, filed Aug. 21, 2014; and "BODY-WORN SENSOR FOR CHARACTERIZING PATIENTS WITH HEART FAILURE," U.S. Ser. No. 14/145,253, filed Jul. 3, 2014, all three of which were incorporated by reference above. The digital processing system 55 within the electronics module 125 digitizes the analog waveforms generated by impedance 50, ECG 51, optical 52, blood pressure 53, and weight 54 systems, and then processes the digitized waveforms using a number of algorithms operating on a microprocessor, as is described in more detail below.

FIGS. 4A-C respectively show a three-dimensional perspective view of the floormat 100 with a patient standing on it. Section views (FIGS. 4B, 4C) better illustrate the back strap 101 and the front strap 103, which cover corresponding portions of the patient's left foot 105a when the patient is using the floormat 100 to measure his or her various physiological parameters.

To measure blood pressure (e.g. SYS and DIA), a diaphragm pump 109 pumps air through a controllable valve 111 and into bladder 107 via a flexible tube 113. The bladder 107 may be provided as a separate bladder "bag" that fits within a pocket in the back strap 101, or it may be formed simply as an airtight chamber within the back strap 101 itself. A pressure sensor 110 that is in fluid (i.e., air) communication with the flexible tube 113 senses pressure within the bladder 107. Collectively, the pump 109, valve 111, and flexible tube 113 form a pressure-delivery system 115 that pumps air into the inflatable bladder 107, thereby causing it to constrict around the patient's left foot 105a; after air inside the bladder reaches a pre-determined pressure, the valve 111 slowly releases pressure. During inflation or deflation, the pressure sensor 110 measures the resultant pressure within the system.

A circuit board 117 with a programmable microprocessor 119 controls operation of the pressure-delivery system 115. Typically, such "control" means switching on and off a transistor (e.g. a field-effect transistor, or FET, not shown in the figure), which causes a voltage (e.g. 5V) to be provided to or removed from the pump 109 and valve 111. Such voltage opens the valve 111 and powers the pump 109, thereby causing it to pump air through the flexible tube 113 and into the bladder 107 to cause the bladder to expand. As the bladder 107 expands, the space inside the rear strap 101 contracts around the bridge of the patient's left foot, thereby constricting blood flow (which is a requirement for measuring blood pressure in this manner, as described in more detail below).

The front strap 103, on the other hand, is positioned to cover a front portion of the patient's left foot 105a and includes the above-referenced optical system 120. The optical system 120 includes a light source 122 and a photodetector 124 that are used to generate a PPG waveform from the top of the patient's foot. The light source 122 may be a light-emitting diode (LED), and the photodetector may be a standard PIN photodetector. During a measurement, the light source 122 emits optical radiation, alternating between red (about 660 nm) and infrared (about 905 nm) wavelengths, to irradiate blood vessels in the front portion of the left foot 105a. Typically with such systems, the radiation propagates a few hundred microns into blood vessels on the foot's outer surface, where it irradiates the vessels and partially reflects back towards the photodetector.

As dictated by Beer's law, which describes the basic premise of optical absorption through a volumetric sample, the reflected radiation will vary in intensity as blood pulses through the vessels and causes them to expand and contract periodically, thus causing the reflected radiation's intensity to modulate. The reflected radiation, in turn, irradiates the photodetector 124, which, in response to the sensed reflected radiation, generates a proportional, modulated photo-induced current that passes through a thin cable 126 to the circuit board 117, where it is amplified and filtered to generate the PPG waveform.

With the physical structure of the floormat 100 in mind, its methods to acquire and process the pressure, PPG, BI, and ECG waveforms, and thereby determine vital signs and hemodynamic parameters, are described in more detail below.

2. Blood Pressure Measurement

Figure 5B:
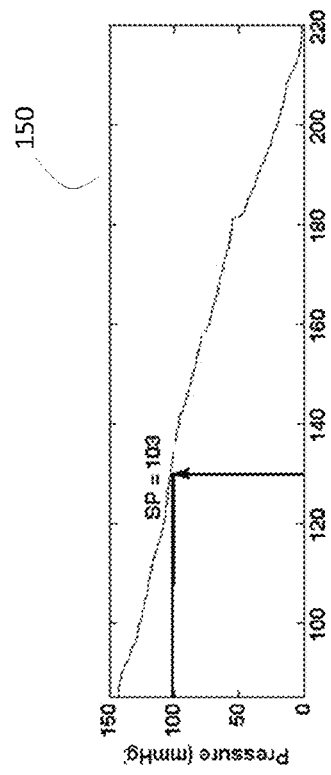
FIG. 5B is a plot illustrating a pressure waveform generated by a blood pressure system within the Floormat of FIG. 1.
Figure 5C:
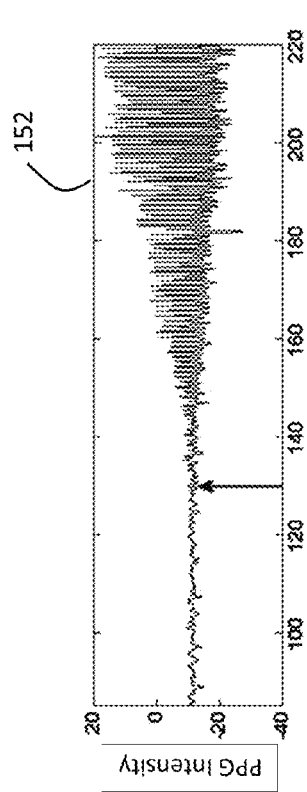
FIG. 5C is a plot illustrating a PPG waveform generated by an optical system within the Floormat of FIG. 1.

To measure blood pressure, e.g., as part of an overall physiological "reading," the pressure-delivery system and the optical system simultaneously measure pressure and blood pulsation and generate time-dependent pressure and PPG waveforms 150, 152 as illustrated in FIGS. 5B and 5C, respectively. These waveforms can be analyzed as the bladder deflates, as is illustrated in the figures. In this case, the optical pulsation in the PPG waveform gradually reappears as the pressure drops below SYS. Alternatively, the waveforms can be measured as the bladder inflates. Here, the pulsation in the waveform gradually diminishes as the pressure approaches SYS. In either case, the microprocessor processes these waveforms with a mathematical model to identify a specific pressure corresponding to the disappearance-point (or reappearance-point) of heartbeat-induced pulsation in the PPG waveform 152.

More specifically, the model assumes that pressure applied by the bladder compresses the arteries in the patient's foot, thereby at least partially occluding blood flow in the arteries. This, in turn, causes the heartbeat-induced pulsation in the PPG waveform to gradually decrease in amplitude during pressurization of the bladder until it (the pulsation) eventually becomes undetectable or, alternatively, to increase in amplitude (if measurement is made during depressurization of the bladder) until it becomes detectable. The pressure being applied to the patient's foot at the moment when pulsation reappears or disappears, as the case may be, corresponds to SYS. A conventional peak-detecting algorithm executing on the microprocessor can be used to detect the onset or cessation of the pulse amplitude in the PPG waveform to identify this "breakpoint;" correlating the breakpoint with the pressure waveform 150 allows the system to make a direct measurement of SYS.

Alternatively, a "fitting" algorithm can be used to model the systematic decrease in pulse amplitude with applied pressure with a mathematical function (e.g. a linear or polynomial function) featuring parameters that are iteratively varied, with the parameters providing the closest approximation to the measured PPG waveform being used to estimate SYS. This latter technique may be used to estimate SYS fairly quickly.

In still other alternative embodiments, pulsations in the pressure waveform caused by heartbeat-induced blood flow in the patient's foot can be analyzed as is done in conventional oscillometry (i.e. the standard technique for automated blood pressure-monitoring systems). Typically, in this case, algorithms process the pressure-dependent amplitude in the pulsations, which are extracted from the pressure waveform with hardware or software filters to remove the DC background. This typically results in a bell-shaped curve from which MAP (corresponding to the curve's maximum point), DIA (extracted from the relatively low-pressure side of the curve), and SYS (extracted from the relatively high-pressure side of the curve) are determined.

Figure 5A:
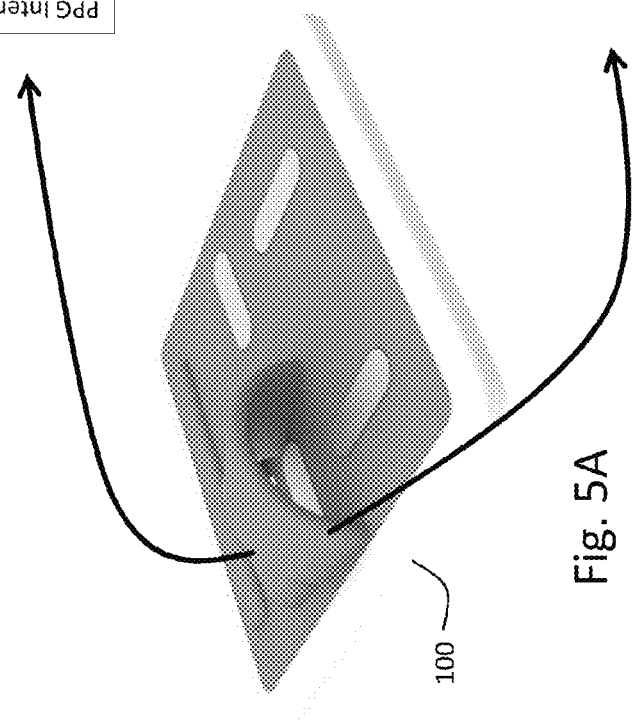
FIG. 5A is a rear perspective view of the floormat shown in FIG. 1.

Referring back to FIG. 5, when pressure applied by the air bladder is roughly equal to the mean pressure within the underlying blood vessel—a condition that causes the heartbeat-induced pulsations to distort the vessels so that their volumetric change is maximized—the pulse amplitude will be maximized. This maximization of the pulse amplitude can, in turn, be detected and therefore used to approximate MAP. Subsequently, DIA is calculated from SYS, MAP (as so approximated), and pulse pressure (PP) using to Eqs. 9 and 10, below.

$$MAP \approx DIA + \tfrac{1}{3} \times PP \qquad (9)$$

$$PP = SYS - DIA \qquad (10)$$

Suitable circuits 160 and 170 to control operation of the pressure-delivery system and the optical system, which work together to measure blood pressure as described above, are illustrated in FIGS. 6B and 6C, respectively.

3. Pulse Oximetry Measurements

In addition to being used to identify the pressure point at which pulsation reappears or disappears as pressure in the air bladder is decreased or increased, respectively, so as to identify SYS, the optical system and its associated electrical circuit 170 are also used to determine pulse oximetry. PPG waveforms generated during this measurement will be similar to those shown in FIG. 5C, only they are measured in the absence of any applied pressure. Thus waveforms for this measurement typically pulsations featuring a relatively constant amplitude.

In general, PPG waveforms are generated using red and infrared radiation. More particularly, the floormat's digital system controls the pulse oximetry circuit 170 so that LEDs 120 (FIG. 4C) operating at red and infrared wavelengths are powered on and off in an alternating fashion. The associated photodetector 124 senses radiation signals reflected from the patient's foot and processes them via the circuit 170 as described below to generate the PPG waveforms.

Thus, during a pulse oximetry measurement, the LEDs alternatingly emit beams of radiation near 660 nm and 905 nm and at approximately 500 Hz. The beams of radiation pass through portions of the foot and rapidly diverge and scatter off of tissue/structures such as skin, bone, and capillaries near the outer surface of the foot before reaching the photodetector. Blood in the capillaries pulsates with each heartbeat and absorbs radiation emitted by the LEDs. This results in separate, time-dependent optical waveforms, i.e., RED/IR(PPG), for each of the 660 nm and the 905 nm radiation. Both waveforms include AC components corresponding to the time-dependent pulsation of the blood and DC components corresponding to time-independent scattering of the radiation off of the skin, bone, and non-pulsating components of the capillaries. Prior to any filtering, the AC component of each signal typically represents about 0.5-1% of the total signal.

Collectively processing the AC and DC signals of the RED/IR(PPG) waveforms allows one to obtain an SpO2 value, and the microprocessor within the floormat uses a number of signal-processing methodologies to do so. Ultimately, the AC and DC components yield a so-called "ratio of ratios" (RoR), which can be related to an SpO2 value through a series of empirically determined coefficients.

In one embodiment of a floormat according to the invention, for example, the RoR is determined by first measuring RED/IR(PPG) waveforms and then passing them through a low-pass filter characterized by a 20 Hz cutoff. The averaged baseline component of each waveform is sampled and stored in memory and represents RED/IR(DC). Both waveforms are additionally filtered with a high-pass filter having a 0.1 Hz cutoff frequency—typically implemented with a finite impulse response function—and finally amplified with a variable gain amplifier. These steps can be implemented with either digital software filters or analog filters integrated into the pulse oximetry circuit 170. Signal components passing through this filter are isolated to yield RED/IR(AC). Once they have been so isolated or extracted, the AC and DC signals are processed to yield a RoR value, described in Eq. 11, which relates to SpO2 as follows:

$$RoR = \frac{RED(AC)/RED(DC)}{IR(AC)/IR(DC)} \qquad (11)$$

An SpO2 value is calculated from Eq. 12, below. Here, coefficients a, b, and c for this calculation are determined beforehand, e.g., by fitting empirical data to a corresponding mathematical function. In one embodiment, coefficients a, b, and c have values, respectively, of 107, −3, and −20.

$$SpO2 = (a + b^*RoR + c^*RoR^2) \times 100 \qquad (12)$$

The exact values of these parameters will depend on and vary with the specific wavelengths of the LEDs used in the pulse oximeter probe. This is because the SpO2 measurement is fundamentally determined by the relative optical absorption of hemoglobin (Hb) and oxygenated hemoglobin (HbO2) in the red and infrared spectral regions, and absorption, in turn, depends on the specific wavelength emitted by a given LED. The absorption spectra of Hb and HbO2 are relatively flat in the infrared spectral region, but strongly divergent in the red spectral region. The coefficients a, b, and c are thus relatively sensitive to the exact wavelength of the red LED. Therefore, prior to manufacturing, a series of empirical studies should be performed using pulse oximeter probes with LEDs that emit radiation of varying wavelengths surrounding the red emission wavelength (e.g. 600-610 nm). A typical example of such a study is called a "breathe-down" study because it involves lowering the SpO2 values of a series of patients (typically about 10-15) under medical supervision. In a breathe-down study, SpO2 is typically lowered by decreasing the amount of oxygen each patient inhales through a specialized ventilator mask; this is often done in a room with a reduced temperature. Blood from the patients is aspirated from an arterial line and analyzed with a blood gas analyzer to determine its oxygen content. Simultaneously, a pulse oximeter probe with known LED wavelengths is attached to each patient—in this case near the feet—and is used to measure the RoR as described in Eq. 11 above. SpO2 values for this experiment, as measured with the blood gas analyzer, typically range from 70-100%. Simultaneous studies are typically done using pulse oximeter probes having LEDs with different red emission spectra. Upon completion of the studies, the wavelength-dependent values of RoR are related to SpO2, as determined by the blood gas analyzer, to calculate coefficients a, b, and c as described above. In general, a different set of coefficients will result for the different LED wavelengths. These coefficients and the optical wavelengths they correspond to, along with a resistor value described below, are stored in a database in memory on the floormat.

4. Stroke Volume, Cardiac Output, and Fluid Measurements

FIGS. 7A-D and 8A-C illustrate in more detail components of the floormat that enable it to measure and generate the patient's BI waveforms and to derive CO/SV values therefrom. As indicated above, two sets of stainless steel electrodes 175a (for the left foot) and 175b (for the right foot) measure electrical signals at the bottoms of the patient's feet. During a measurement, an impedance circuit 220 (FIG. 8C) injects high-frequency, low-amperage current (I) through the rear, "heel electrodes" 130a, 130b (see FIGS. 2A and 2B), which are positioned to make contact with the bottoms of the patient's left and right heels when he or she stands on the floormat. Suitably, the modulation frequency may be about 70-100 kHz, and the current may be about 4-10 mA. Furthermore, the current injected by one electrode is out of phase by 180° with respect to the current injected by the other electrode.

Circuitry within the floormat is configured such that the current injected by each heel electrode flows up the corresponding leg, through the patient's abdomen/thorax, down the other leg, and to the opposite foot. As the current flows, it scatters off the tissue it propagates through, and encounters static (i.e. time-independent) resistance from body components such as bone, skin, and other tissue in the patient's lower extremities. Additionally, blood conducts current to some extent; therefore, blood ejected from the left ventricle of the heart and into the aorta provides a dynamic (i.e. time-dependent) component of electrical conductivity and, consequently, electrical resistance. The aorta is the largest artery passing blood out of the heart, and thus it has a dominant impact on the dynamic resistance; other vessels, such as the superior vena cava, will contribute in a minimal way to the dynamic resistance.

Forward electrodes 129a, 129b (see FIGS. 2A and 2B), on the other hand, are positioned so as to contact the balls of the patient's left and right feet, respectively, when the patient stands on the floormat. These forward electrodes sense, and hence measure, a time-dependent voltage (V) that varies with the resistance (R) encountered by the injected current I according to Ohm's Law (V=I×R). During a measurement, the time-dependent voltage sensed by the forward electrodes is amplified and filtered by the impedance circuit 220 and ultimately processed with an analog-to-digital converter in the electronics module.

Two further waveforms can be extracted from the BI waveform. The first waveform 180 (FIG. 7C) exhibits relatively high-frequency variations caused by heartbeat-induced impedance changes measured by the BI system. This represents the AC component of the BI bioimpedance waveform. Furthermore, the mathematical derivative of the AC component of the BI waveform (plot 182, FIG. 7D) can be processed with a first algorithm to determine $(dZ(t)/d(t))_{max}$ and left ventricular ejection time (LVET). (As used herein, $d(Z(t))/dt$ and $d(BI(t))/d(t)$ are considered to be equivalent.) A separate waveform—not shown in the figure but exhibiting relatively low-frequency variations in impedance—can be processed with a second algorithm to determine $Z_0$. These three parameters—$(dZ(t)/d(t))_{max}$, LVET, and $Z_0$—are then processed to calculate SV using an equation such as that shown in Eq. 13, which is Sramek-Bernstein equation, or a mathematical variation thereof.

$$SV = \delta \frac{L^3}{4.25} \frac{(dZ(t)/dt)_{max}}{Z_o} LVET \qquad (13)$$

In Eq. 13, the term "Z(t)" represents the AC component of a conventional impedance waveform. According to the invention described herein, Z(t) is replaced with the AC component of the BI waveform. δ represents compensation for body mass index, which may be determined using the floormat's weight scale component, as described in more detail below. $Z_0$ is a base impedance value estimated from the DC component of the BI waveform. L is estimated from the distance separating respective current-injecting and voltage-measuring electrodes, and can be approximated from the patient's height.

Alternatively, waveforms measured with the impedance system can be processed with an algorithm based on Eqs. 5 and 6, above.

And LVET, as described above, is the left ventricular ejection time, which is preferably determined from the BI waveform, or alternatively from the HR using an equation called "Weissler's Regression," shown below in Eq. 14, which estimates LVET from HR:

$$LVET = -0.0017 \times HR + 0.413 \qquad (14)$$

Weissler's Regression allows LVET to be estimated from HR as determined from the ECG waveform. This equation and several mathematical derivatives, along with the parameters shown in Eq. 13, are described in detail in the following reference, the contents of which are incorporated herein by reference: Bernstein, *Impedance cardiography: Pulsatile blood flow and the biophysical and electrodynamic basis for the stroke volume equations*; J Electr Bioimp; 1: 2-17 (2010). Both the Sramek-Bernstein Equation and an earlier derivative of it, called the Kubicek Equation, feature a "static component" $Z_0$ and a "dynamic component" $\Delta Z(t)$, which relates to LVET, and a $(dZ/dt)_{max}/Z_0$ value, calculated from the derivative of the raw bioimpedance signal, $\Delta Z(t)$. (These equations assume that $(dZ(t)/dt)_{max}/Z_0$ represents a radial velocity (with units of Ω/s) of blood due to volume expansion of the aorta.)

Figure 7D:
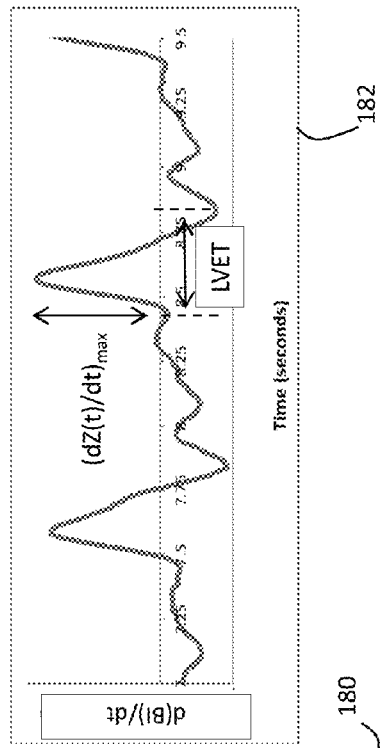
FIG. 7D is a time-dependent plot of a derivatized BI waveform of FIG. 7C.
Figure 7A:
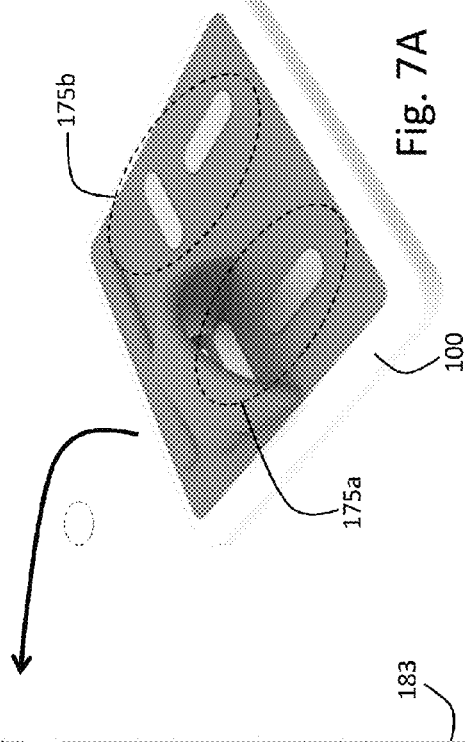
FIG. 7A is a rear perspective view of the floormat shown in FIG. 1.
Figure 7C:
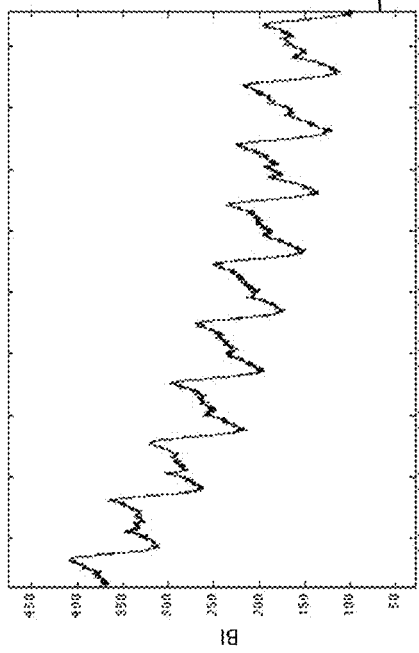
FIG. 7C is a time-dependent plot of a bioimpedance (BI) waveform generated with the floormat of FIG. 7A.
Figure 7B:
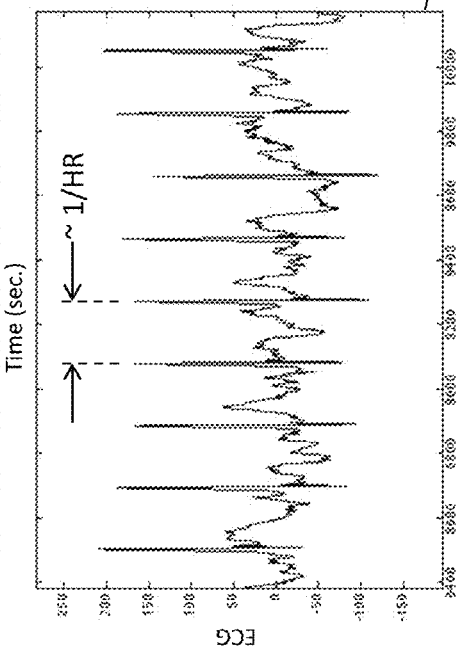
FIG. 7B is a time-dependent plot of an ECG waveform generated with the floormat of FIG. 7A.

Additionally, the same electrodes used to measure the impedance waveforms BI can also be used to measure standard ECG waveforms, which are illustrated in the plot 183 (FIG. 7B). Associated electrical circuitry 230 used to determine the ECG waveform is illustrated in FIG. 8B. From this waveform, HR can be estimated from the inverse of the RR interval, as indicated on the plot 183.

5. Pulse Transit Time Measurements

Pulse transit times are timing-related parameters that can be extracted from the physiological waveforms described above. They are known to correlate inversely to blood pressure and, additionally, may indicate the compliance (and thus stiffness) of the patient's arteries. In certain embodiments, the floormat can measure pulse transit times, as explained in more detail below, and then use these parameters to estimate blood pressure without using a pressure-delivery system like the one described above. Additionally, pulse transit times, combined with blood pressure values determined using the pressure-delivery system, may be used to estimate changes in the patient's arterial compliance. One technique for making such an estimation is described in detail in the following reference, the contents of which are incorporated herein by reference: "Vital sign monitor for cufflessly measuring blood pressure corrected for vascular index," Publication number WO2008154647, filed Jun. 12, 2008.

FIG. 9, for example, shows the following time-dependent waveforms, as measured by the floormat: ECG (plot 200), BI (plot 202), PPG (plot 204), d(BI)/dt (plot 206), and d(PPG)/dt (plot 208). As shown in plots 200 and 202, individual heartbeats produce time-dependent pulses in both the ECG and BI waveforms. As is clear from the data, pulses in the ECG waveform precede those in the BI waveform. The ECG pulses—each featuring a sharp, rapidly rising QRS complex—indicate initial electrical activity in contractions in the patient's heart and, informally, the beginning of the cardiac cycle.

BI pulses follow the QRS complex by about 100 ms and indicate blood flow through arteries in the region of the body where the electrodes make contact with the skin. During a heartbeat, blood flows from the patient's left ventricle into the aorta; the volume of blood that leaves the ventricle is the SV. Blood flow periodically enlarges this vessel, which is typically very flexible, and also temporarily aligns blood cells (called erythrocytes) from their normally random orientation. Both the temporary enlargement of the vessel and alignment of the erythrocytes improves blood-based electrical conduction, thus decreasing the electrical impedance as measured with BI. The d(BI)/dt waveform (plot 206) shown in FIG. 9 is a first mathematical derivative of the raw BI waveform, meaning its peak represents the point of maximum impedance change.

A variety of time-dependent parameters can be extracted from the ECG and BI waveforms. For example, as noted above and indicated in FIG. 7B, it is well know that HR can be determined from the time separating neighboring ECG QRS complexes. Likewise, LVET can be measured directly from the derivative of the BI pulse, as shown in FIG. 7D, and is determined from the onset of the derivatized pulse to the first positive-going zero crossing. Also measured from the derivatized BI pulse is $(dBI/dt)_{max}$, which is a parameter used to calculate SV as described above.

The time difference between the ECG QRS complex and the peak of the derivatized BI waveform represents a pulse arrival time PAT, as indicated in FIG. 9. This value can be calculated from other fiducial points, including, in particular, locations on the BI waveform such as the base, midway point, or maximum of the heartbeat-induced pulse. Typically, the maximum of the derivatized waveform is used to calculate PAT, as it is relatively easy to develop a software beat-picking algorithm that finds this fiducial point.

PAT correlates inversely to SYS and DIA, as shown below in Eqs. 15 and 16, where $m_{SYS}$ and $m_{DIA}$ are patient-specific slopes for SYS and DIA, respectively, and $SYS_{cal}$ and $DIA_{cal}$ are values of SYS and DIA, respectively, measured during a calibration measurement. (Such a measurement can, for example, be performed with the pressure-delivery and optical systems described above.) Without the calibration, PAT only indicates relative changes in SYS and DIA. The calibration yields both the patient's immediate values of SYS and DIA. Multiple values of PAT and blood pressure can be collected and analyzed to determine patient-specific slopes $m_{SYS}$ and $m_{DIA}$, which relate changes in PAT with changes in SYS and DIA. The patient-specific slopes can also be determined using pre-determined values from a clinical study, and then combining these measurements with biometric parameters (e.g. age, gender, height, weight) collected during the clinical study.

$$SYS = \frac{m_{SYS}}{PAT} + SYS_{cal} \quad (15)$$

$$DIA = \frac{m_{DIA}}{PAT} + DIA_{cal} \quad (16)$$

In embodiments of the floormat, waveforms like those shown in FIG. 9 can be processed to determine PAT. This parameter, combined with a calibration determined as described above, can be used by the floormat to determine blood pressure without a physical-pressure-applying mechanism via Eqs. 15 and 16, above. Typically PAT and SYS correlate better than PAT and DIA, and thus this parameter is first determined using Eq. 15. In one embodiment, DIA is then determined using Eq. 16. Alternatively, PP can be estimated from SV, as described below, and then used with SYS to determine DIA according to, e.g. Eqs. 5 or 6, above.

PP can be estimated from either the absolute value of SV, SV modified by another property (e.g. LVET), or the change in SV. In the first method, a simple linear model is used to process SV (or, alternatively, SV×LVET) and convert it into PP. The model uses the instant values of PP and SV, determined as described above from a calibration measurement, along with a slope that relates PP and SV (or SV×LVET) to each other. The slope can be estimated from a universal model that, in turn, is determined using a population study.

Alternatively, a slope tailored to the individual patient can be used. Such a slope can be selected, for example, using biometric parameters describing the patient as described above.

Here, PP/SV slopes corresponding to such biometric parameters are determined from a large population study and then stored in computer memory on the floormat. When a floormat is assigned to a patient, their biometric data is entered into the system, e.g. using a GUI operating on mobile telephone, that transmits the data to a microprocessor in the floormat via Bluetooth®. Then, an algorithm on the floormat processes the data and selects a patient-specific slope. Calculation of PP from SV is explained in the following reference, the contents of which are incorporated herein by reference: "*Pressure-Flow Studies in Man. An Evaluation of the Duration of the Phases of Systole*," Harley et al., *Journal of Clinical Investigation*, Vol. 48, p. 895-905, 1969. As explained in this reference, the relationship between PP and SV for a given patient typically has a correlation coefficient r that is greater than 0.9, which indicates excellent agreement between these two properties. Similarly, in the above-mentioned reference, SV is shown to correlate with the product of PP and LVET, with most patients showing an r value of greater than 0.93 and the pooled correlation value (i.e., the correlation value for all subjects) being 0.77. This last value indicates that a single linear relationship between PP, SV, and LVET may hold for all patients.

More preferably, PP is determined from SV using relative changes in these values. Typically, the relationship between the change in SV and change in PP is relatively constant across all subjects. Thus, similar to the case for PP, SV, and LVET, a single, linear relationship can be used to relate changes in SV and changes in PP. Such a relationship is described in the following reference, the contents of which are incorporated herein by reference: "*Pulse pressure variation and stroke volume variation during increased intra-abdominal pressure: an experimental study*," Didier et al., *Critical Care*, Vol. 15:R33, p. 1-9, 2011. Here, the relationship between PP variation and SV variation for 67 subjects displayed a linear correlation of r=0.93, which is an extremely high value for pooled results that indicates a single, linear relationship may hold for all patients.

From such a relationship, PP can be determined from the BI-based SV measurement, and SYS can be determined from PAT. DIA can then be calculated from SYS and PP.

The floormat determines RR from the DC BI waveform, described above. In this case, the patient's respiratory effort moves air in and out of the lungs, thus changing the impedance in the thoracic cavity. This time-dependent change maps onto the BI waveform, typically in the form of oscillations or pulses that occur at a much lower frequency than the heartbeat-induced cardiac pulses shown in the upper part of FIG. 10. Simple signal processing (e.g. filtering, beat-picking) of the low-frequency, breathing-induced pulses in the waveform yields RR.

Another parameter, called vascular transit time (VTT), can be determined from pulsatile components in the BI (or d(BI)/dt) waveform and the PPG (or d(PPG)/dt) waveform. FIG. 9 shows in more detail how VTT is determined. It can be used in place of PAT to determine blood pressure, as described above. Using VTT instead of PAT in this capacity offers certain advantages, namely, lack of signal artifacts such as pre-injection period (PEP) and isovolumic contraction time (ICT), which contribute components to the PAT value but which are not necessarily sensitive to or indicative of blood pressure.

6. Weight, Percent Body Fat, and Muscle Mass Measurement

In addition to the vital signs and hemodynamic parameters described above, the floormat also measures biometric parameters such as weight, percentage body fat, and muscle mass (also known as skeletal muscle). Weight is measured using a relatively conventional scale mechanism within the floormat. As illustrated in FIGS. 10A-D, for example, embodiments of the floormat 100 include a stabilizing bar 150 with one or more load cells 148 attached to it to measure the patient's weight. The stabilizing bar 150, which may have holes 154 extending through it (FIG. 10C) to reduce its rigidity and allow it to flex/induce strain when a patient stands on the floormat, is suitably disposed on the floormat's bottom surface and connected to the supporting posts 104a, 104b at its distal ends. In some embodiments of the floormat, the floormat 100 may have two stabilizing bars, with one stabilizing bar (as illustrated) being connected to supporting posts 104a, 104b on one side of the floormat and the other stabilizing bare (not illustrated) being connected to supporting posts (also not illustrated) located at the floormat's opposite corners. In the illustrated embodiment, the two stabilizing bars are parallel to each other; in alternate embodiments of the floormat, they may intersect with each in a criss-cross pattern.

As further illustrated in the figures, load cell 148 is located near the mid-point of the stabilizing bar and is integrated directly into the stabilizing bar, and a pair of strain gauges 151, 152 are connected to opposite surfaces of the stabilizing bar 150 to form the load cell 148 portion of the stabilizing bar. In one embodiment of the floormat, the strain gauges may be flexible circuits with a serpentine pattern of conductive traces having a resistance value that varies with strain. When the patient stands on the floormat, the stabilizing bar flexes or bows; depending on the specific manner in which the stabilizing bar is mounted and supported within the base of the floormat, it will bow either upwardly (concavity-down) or downwardly (concavity-up). With such flexing of the stabilizing bar, the strain gauge located on the "inside" surface of the bow will be compressed, while the strain gauge located on the "outside" surface of the bow will be extended. Both compression and extension of the strain gages cause slight changes in the strain gauges' resistance values—one change being a decrease in resistance and the other change being an increase in resistance—and such variation in resistance can be measured and used to determine the amount by which the stabilizing bar flexes and, hence, the weight being applied to it.

In alternate embodiments, the strain gauges shown in FIG. 10 can be disposed in other locations within the floormat. In one alternate configuration, for example, they are disposed in the floormat's support posts 104a, 104b, and configured so that a patient standing on the floormat causes them to compress and extend, as described above.

In total, the illustrated embodiment of a floormat according to the invention has two load cells—one for each stabilizing bar—and thus four strain gauges. As illustrated in FIG. 10D, each of the strain gauges forms an arm of an electrical circuit 160 featuring a four-resistor circuit component (i.e., a Wheatstone Bridge 162) that, when connected to an amplifier circuit 164, can be used to determine the patient's weight.

During a measurement, the patient stands on the top surface 102 of the floormat 100. The force associated with the patient's weight affects the strain gauges, resulting in small resistance changes that are amplified by the Wheatstone Bridge 162, causing it to produce an output voltage. The output voltage is further amplified by the amplifier circuit 164, thus resulting in an input voltage to an analog-to-digital converter that varies with weight. (Gain resistor RG determines the degree of amplification in the amplifier circuit 164.) The system can be calibrated by placing weights of known values on the floormat's surface and then measuring the resulting voltages that are input to the analog-to-digital converter. Once the load-cell system has been calibrated, the floormat can measure the patient's weight.

The floormat complements this weight measurement by estimating the patient's percent body fat and muscle mass. This measurement is implemented with the four stainless steel electrodes 129a, 129b, 130a, and 130b (see, e.g., FIGS. 2A and 2B) that contact the soles of the patient's feet. More specifically, as addressed above, these electrodes measure electrical signals to generate electrical impedance waveforms $Z_0$ and $\Delta Z(t)$. $Z_0$, in particular, is an input into Eq. 16, below, and is used to determine percentage of body fat. Additionally, the floormat may include another circuit that measures a parameter called bio-reactance (Xc), which is also used as an input in Eq. 16. (Bio-reactance refers to the electrical resistive, capacitive, and inductive properties of blood and biological tissue that induce phase shifts between an applied electrical current and the resulting voltage signal. This parameter is distinguished from bioimpedance, addressed above, which refers to the electrical properties of blood and tissue that determine the amplitude of the voltage field resulting from an applied electrical current.)

During a measurement, the stainless steel electrodes measure electrical signals that are processed with circuitry in the floormat to determine $Z_0$ (from the bioimpedance measurement used to sense BI waveforms) and Xc (from the bioreactance measurement, described above). These parameters are used in Eq. 16, below, along with the patient's weight as measured by the weight-measuring system, to estimate the patient's fat-free mass (FFM), which can be used as an estimate of muscle mass:

$$FFM(kg) = a \times (\text{height}^2/Z_0) + b \times (\text{weight}) - c \times (\text{age}) + d \times X_c) - e \quad (16)$$

where a, b, c, and d are constants determined from a clinical study, as follows: a=0.7374, b=0.1763, c=0.1773, d=0.1198, and e=2.4658. Eq. 11, along with the constants used to estimate FFM, are described in detail in the following reference, the contents of which are incorporated herein by reference: Macias et al., *Body fat measurement by bioelectrical impedance and air displacement plethysmography: a cross-validation study to design bioelectrical impedance equations in Mexican adults*; Nutrition Journal; 6: (2007). Subtracting FFM from body weight, and then dividing this number by the body weight, is used to estimate the patient's percentage of body fat.

7. Electrode Placement and Impedance Measurements with the Floormat

In the floormat embodiments described so far, all four electrodes—i.e., the two current-injecting electrodes and the two current-receiving/voltage-sensing electrodes—are arranged on the upper surface of the floormat so that all skin-to-electrode contact occurs on the soles of the patient's feet and current flows from one foot to the other in connection with the BI measurement. As noted above, however, in alternate embodiments of the floormat, a handheld electrode unit (featuring two electrodes) can be provided in addition to or instead of one of the foot-contacting electrode pairs, so that current flows between one of the feet and one of the hands. The current-flow pathway for each such configuration is illustrated in FIGS. 11A and 11B.

Thus, as shown in FIG. 11A for a foot-to-foot configuration of the floormat, electrode pairs 252, 254—each pair including a current-injecting electrode ($I_1$, $I_2$) and a voltage-sensing electrode ($V_1$, $V_2$)—contact the soles of the feet of the patient 250, and the current-injecting electrodes $I_1$ and $I_2$ inject high-frequency (e.g. 70 kHz), low-amperage (e.g. 4 mA) current into the patient's feet. The current injected by each electrode is suitably out of phase by 180° with respect to the current injected by the other electrode. Electrode $V_1$ measures the resistance (or impedance) encountered by the propagating current injected by electrode $I_2$ (as a voltage, per Ohm's Law), and electrode $V2_2$ measures the resistance (or impedance) encountered by the propagating current injected by electrode $I_1$.

As current propagates through the patient's body, it scatters off of bone, skin, organs, etc., as indicated by the meandering line 258 shown in the figure. Typically, such tissue has static electrical impedance properties, i.e., properties that are relatively constant in time. Thus, they contribute to a "background" or DC signal component in the BI measurement.

On the other hand, in contrast, tissue in a region 256 near the chest contains physiological components that vary with time and thus contribute to a variant or AC signal component in the BI measurement. For example, blood, which is a relatively good electrical conductor, flows from the left ventricle into the aorta with each heartbeat, and its contribution to the BI signal is a heartbeat-induced pulsatile signal, called an impedance plethysmogram, such as that shown in FIG. 7C. Blood flowing in other vessels will also contribute to the amplitude of pulses in the plethysmogram, but the contribution from the aorta is predominant, as noted above. Furthermore, fluid such as lung fluid in the region 256 also conducts electricity, and thus contributes to the BI signal. However, such fluid levels vary relatively slowly (i.e., much slower that pulsatile blood flow), and thus changes in this signal component occur on a much slower time scale.

With a floormat configuration like that described above, where all four electrodes are located on the upper surface of the floormat, current (indicated by the line 258) propagates from one foot to the other through a somewhat circuitous path and may have limited presence in the region 256 responsible for AC components of the BI signal due, for example, to time-dependent physiological events such as heartbeat-induced blood flow and fluid change.

However, as illustrated in FIG. 11B, if one of the pairs 254 of electrodes (e.g., $I_2$ and $V_1$) are placed near the hand, the region 256 responsible for AC contributions to the BI signal is exposed to a relatively large amount of injected current and thus may yield a stronger signal BI, especially as it relates to blood and fluid flow. Thus, a floormat embodiment that includes electrodes that contact the patient's feet and a hand, as described in more detail, may be preferred in some circumstances.

8. Mechanical Form Factors for the Floormat

FIGS. 12-14 show different embodiments of a floormat according to the invention that include electrodes which contact both the hands and feet. As shown in FIGS. 12A and 12B, in some embodiments, the floormat 300 features a base portion 319 and a hand-held portion 318. The base portion 319 includes a pair of electrodes 312, 314 that serve, respectively, as single current-injecting (i.e., $I_x$) and voltage-measuring (i.e., $V_x$) electrodes, as described above. The same electrodes are used to measure ECG waveforms and bioreactance signals, which, as described above are used to estimate percent body fat and muscle mass. Typically, the electrodes are located on the floormat's top surface 317, usually made from a silicone rubber, and are disposed where the patient's right foot would rest during a measurement.

The top surface 317 also supports an air-filled bladder 316 and an electronics module 310. The air-filled bladder 316 receives the patient's left foot 320 during a measurement, and it is similar to that shown in FIG. 4A-C. During a measurement, a pressure-delivery system, similar to that described above, inflates and then deflates the air-filled bladder 316 as part of a blood pressure measurement.

Within the air-filled bladder 316 is an optical system featuring a light source and a photodiode that, collectively, measure PPG waveforms using LEDs that emit in both the red and infrared spectral regions, as described above. The PPG waveform is processed as described above to measure both blood pressure and SpO2. The electronics module 310 includes analog electronics to determine the BI, ECG, PPG, and pressure waveforms, along with digital electronics such as an analog-to-digital converter, microprocessor, and Bluetooth® system for processing these waveforms to determine physiological parameters and then transmitting the physiological parameters and waveforms to a mobile device 307, e.g., a smartphone or tablet computer.

The hand-held portion 318 connects through and is supported by a hollow pole 301 extending from the base portion 319. The hand-held portion 318 includes complementary current-injecting electrodes 303, 305 and voltage-measuring electrodes 302, 304 that work in concert with those electrodes 312, 314 in the base portion 319. The hand-held portion 318 also includes a mounting platform 307 to support the patient's mobile phone 306 during a measurement. Because they make a differential measurement, the current-injecting electrodes 303, 305 are wired together, as are the voltage-measuring electrodes 302, 304. In this way, each wired pair functions essentially as a single electrode.

During a measurement, the patient holds on to the hand-held portion 318 so that the current-injecting electrode 303 and the voltage-measuring electrode 302 are contacted by the patient's left hand, and the complementary current-injecting electrode 305 and voltage-measuring electrode 304 are contacted by the patient's right hand. The mounting platform 307 supports the patient's mobile phone 306 so that it is near eye level and easy to see. A standard, flexible cable (not shown in the figure) connects to the electrodes 302, 303, 304, 305 and passes through the hollow pole 301, where it connects to a corresponding circuit in the electronics module 310, along with a similar cable extending from the electrodes 312, 314 in the base portion 319.

A GUI operating on the mobile device 307 guides the patient through a measurement and, in turn, displays waveforms and physiological parameters as described above. Once the measurement is complete, the mobile device 307 transmits any numerical values and/or waveforms through a second wireless interface, e.g. WiFi® or cellular system, to a cloud-based system, as illustrated schematically in FIG. 1.

Suitably, the hollow pole 301 shown in the figure is somewhat rigid and thus, for example, helps stabilize the patient and potentially keeps them from falling over during a measurement.

For an alternate embodiment of the floormat 350, as shown in FIGS. 13A, 13B, the hollow pole of FIG. 12A, 12B can be replaced by a flexible cable 351. The flexible cable 351 is essentially the same as the flexible cable referenced with respect to FIG. 12A, 12B. Unlike the hollow pole 301, however, the flexible cable 351 provides essentially no mechanical support to the patient. However, its flexible nature means it can be moved around easily during a measurement, and it is ideally suited to be held by patients of a variety of heights.

In still another embodiment of the invention, as shown in FIG. 14A, 14B, the floormat 450 features a flexible cable 451 that connects to a hand-held portion 418 designed for just a single hand. The hand-held portion 418 includes a grip 453 featuring a single current-injecting electrode 454 and a single voltage-measuring electrode 452. The electrodes 452, 454 connect to the electronics module 310 in the base portion 319 through a flexible cable 451 similar to that described above, but only containing wires for just the single electrodes 452, 454. In this case, the hand-held portion 418 lacks any type of mount for the mobile device.

Figure 15:
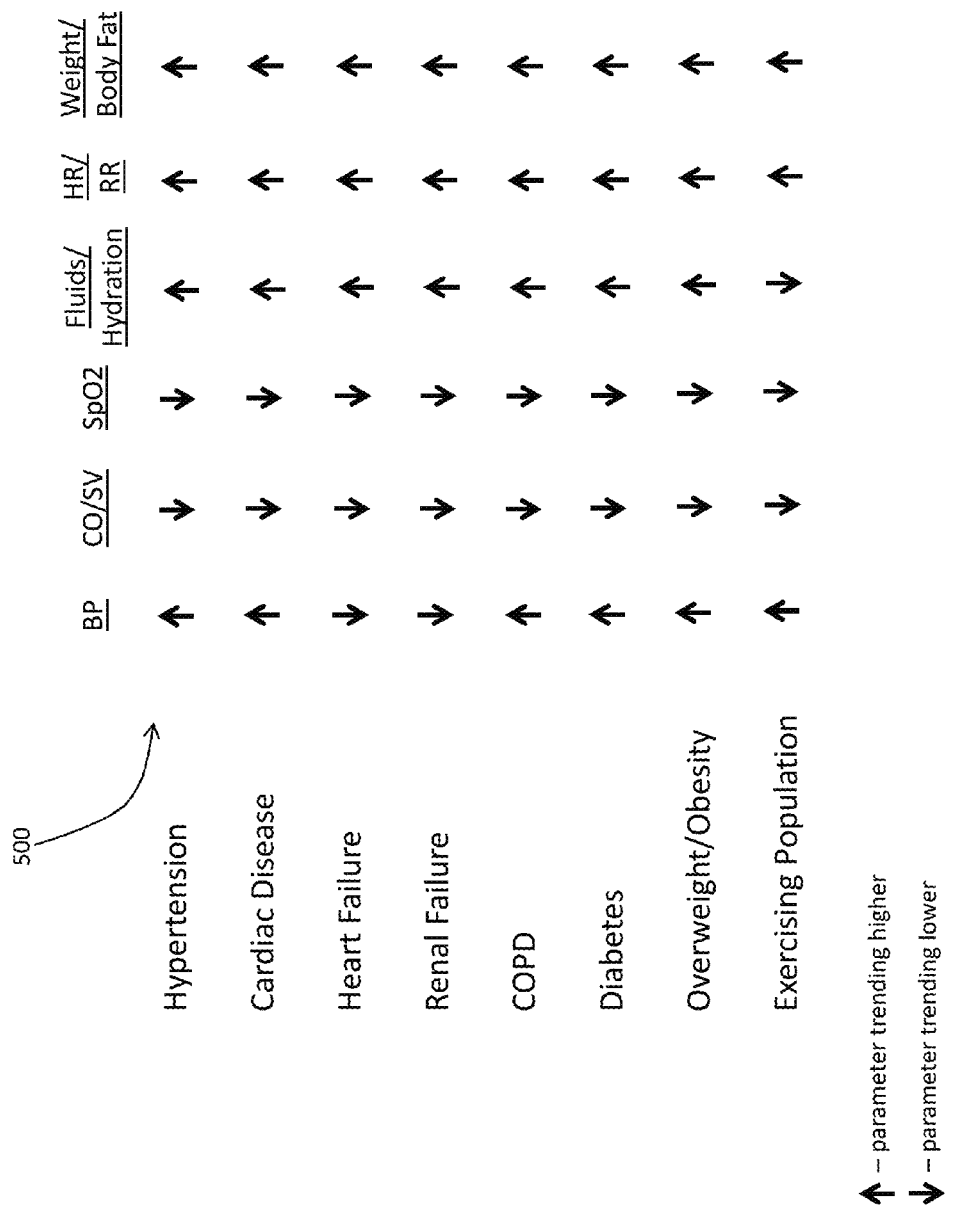
FIG. 15 is a table showing how parameters measured by the floormat trend with specific disease states and populations.

In general, the overarching purpose of a floormat according to the invention, as described above, is to make daily measurements of a wide range of physiological parameters that, in turn, can be analyzed to diagnose specific disease states. It is often the time-dependent trends in the physiological parameters that provide the best indication of such disease states. At a simple level, for example, a patient's weight value of 200 pounds his limited clinical value by itself. However, a weight value that rapidly increases from 200 to 210 pounds over a period of a few days may indicate the onset of a disease, such as CHF. In general, it is a collection of trends in multiple physiological parameters that often serve as the best marker for the onset of disease states. In this regard, FIG. 15 shows, for example, a table 500 indicating how trends in different physiological parameters can be used to diagnose disease states such as hypertension, cardiac disease, heart failure, renal failure, chronic obstructive pulmonary disease (COPD), diabetes, and obesity. In addition, the table 500 indicates how such trends may show beneficial progress to a population actively involved in exercise.

Embodiments other than those described above are within the scope of the invention. For example, the mechanical configuration of the floormat can take many shapes. In one embodiment, the floormat has a mechanical configuration similar to that of a conventional weight scale. Here, it may feature a rigid base, four distinct feet, and a cross-sectional shape that is relatively square. In an alternative embodiment, the floormat may feature the mechanical configuration of a conventional yoga mat and would be made with a flexible material (e.g. foam or silicone rubber) that can be easily rolled. In that case, electronic components required to measure all of the above-mentioned parameters would be embedded in the flexible material and may connect through flexible electronics, e.g. a flex circuit made from a polymeric material such as Kapton. Or the floormat may feature a rigid base and a surrounding flexible portion that can be removed, washed, and customized for the patient. Other mechanical configurations are also possible, such as one that includes foot-worn enclosures, e.g. something resembling a slipper, sandal, or shoe. In that case, electronics would be embedded in the soles of the foot-worn enclosures, which would typically connect to each other with a wire or flexible circuit.

In a preferred embodiment such as the one described above, the floormat does not feature a display. Omission of a display reduces costs and complexity associated with manufacturing and simplifies the floormat's design. Additionally, most patients using the floormat will have a conventional mobile device, such as a smartphone or tablet, and such devices typically have high-resolution displays (e.g., those featuring organic LED or liquid crystals) that are driven by sophisticated operating systems, and such systems can easily display all the numerical and waveform information generated by the floormat.

Alternatively, the floormat may include a simple display, e.g., one that displays basic waveform information. In most cases, the floormat will include one or more colored LEDs that indicate its overall status, e.g., its battery power; whether or not a measurement is ready to start or is complete; and if an error was present during the measurement.

Sensors and electronics other than those described above can be used for the floormat. For example, while a Wheatstone Bridge is a conventional circuit for measuring weight, this sensor can be replaced by something more suitable to the floormat's form factor, e.g., a thin, pressure-sensitive resistor such as that manufactured by Tekscan (www.tekscan.com). Likewise, the circuitry described above for measuring BI, ECG, and PPG waveforms can be replaced by an alternative circuit that performs a similar function. Furthermore, wireless transmitters, e.g. the Bluetooth®, WiFi®, and cellular transmitters described above, can be replaced by other short- or long-range radios that perform essentially the same function.

Other sensors not described in detail above may be incorporated into the floormat. For example, the hand-held component shown in FIGS. 12-14 may include other sensing components. In various embodiments, the hand-held component may include an optical system similar to that described above. This may be used, for example, to measure SpO2 values and PPG waveforms from the hands or fingers. The PPG waveforms may then be used to calculate PAT and VTT and then used to measure blood pressure, as described above. In still other embodiments, the hand-held component may include a spirometer or end-tidal CO2 sensor to measure respiration rate, expelled gasses, and respiratory effort. The hand-held component may also include a glucometer for measuring glucose levels in the patient's blood or an ultrasound sensor for taking simple, Doppler-type images from the patient. In other embodiments, the hand-held component may include a camera for taking a picture of the patient or a portion of the patient, e.g., a lesion or a growth. In other embodiments, the floormat may link to other conventional wearable devices, such as devices that track a patient's activity and/or HR during exercise or devices such as ambulatory blood pressure monitors.

The GUI operating on the mobile device may serve many different functions. As described above, its primary function is to display numerical and waveform information from the patient. Additionally, it may: i) display trends in these values; ii) indicate a particular disease state (such as those listed in the table shown in FIG. 15); iii) prompt the patient to step on the floormat; iv) link the floormat to a website involving social media or to a website viewable by family, friends, or a pre-approved clinician; v) provide guidance to the patient on managing their condition; vi) be used to enter biometric information that is not measurable by the floormat, such as the patient's age, height, race, or gender; vii) estimate and render the patient's physical age (based on parameters such as body-mass index and HR); viii) track the patient's performance vs. goals; ix) compare data measured from the patient to other data (e.g. in their age group) to promote competition; and x) show advertisements from relevant vendors. Other software-based applications are, of course, possible with the mobile device and its associated GUI.

In other embodiments, the floormat described above can integrate with a 'patch' that directly adheres to a portion of a patient's body, or a 'necklace' that drapes around the patient's neck. The patch would be similar in form to the necklace's base, although it may take on other shapes and form factors. It would include most or all of the same sensors (e.g. sensors for measuring ECG, TBI, and PPG waveforms) and computing systems (e.g. microprocessors operating algorithms for processing these waveforms to determine parameters such as HR, HRV, RR, BP, SpO2, TEMP, CO, SV, fluids) as the base of the necklace. However unlike the system described above, the battery to power the patch would be located in or proximal to the base, as opposed to the strands in the case of the necklace. Also, in embodiments, the patch would include a mechanism such as a button or tab functioning as an on/off switch. Alternatively, the patch would power on when sensors therein (e.g. ECG or temperature sensors) detect that it is attached to a patient.

In typical embodiments, the patch includes a reusable electronics module (shaped, e.g., like the base of the necklace) that snaps into a disposable component that includes electrodes similar to those described above. The patch may also include openings for optical and temperature sensors as described above. In embodiments, for example, the disposable component can be a single disposable component that receives the reusable electronics module. In other embodiments, the reusable electronics module can include a reusable electrode (made, e.g., from a conductive fabric or elastomer), and the disposable component can be a simple adhesive component that adheres the reusable electrode to the patient.

In preferred embodiments the patch is worn on the chest, and thus includes both rigid and flexible circuitry, as described above. In other embodiments, the patch only includes rigid circuitry and is designed to fit on other portions of the patient's body that is more flat (e.g. the shoulder).

In embodiments, for example, the system described above can calibrate the patch or necklace for future use. For example, the floormat can determine a patient-specific relationship between transit time and blood pressure, along with initial values of SYS, DIA, and MAP. Collectively these parameters represent a cuff-based calibration for blood pressure, which can be used by the patch or necklace for cuffless measurements of blood pressure. In other embodiments, the floormat can measure a full-body impedance measurement and weight. These parameters can be wirelessly transmitted to the necklace or patch, where they are used with their impedance measurement to estimate full-body impedance (e.g. during a dialysis session). Additionally, during the dialysis session, the necklace or patch can use the values of full-body impedance and weight to estimate a progression towards the patient's dry weight.

These and other embodiments of the invention are deemed to be within the scope of the following claims.

What is claimed is:

1. A system for measuring a blood pressure value from a patient, comprising:
    a base comprising a bottom surface configured to rest on or near a substantially horizontal surface, and a top surface configured to receive at least one of the patient's feet;
    a cuff-based system, mounted directly on the base and configured to receive a foot from the patient, comprising an inflatable bladder configured to apply pressure to a portion of the foot and analyzes the applied pressure to determine a blood pressure calibration value;
    an electrical impedance system connected to the top surface, the electrical impedance system comprising at least four electrodes, with a first electrode configured to inject an electrical current into the patient's feet, and a second electrode configured to measure a first set of signals induced by the electrical current and representative of an impedance plethysmogram;
    a heart rate monitoring system connected to the top surface and comprising a differential amplifier connected to an electrode that can be either the second electrode or a new, third electrode, the differential amplifier configured to measure a second set of signals representative of a cardiac rhythm from the patient; and
    a processing system in electrical contact with the electrical impedance system and the heart rate monitoring system, and configured to: 1) receive the first set of signals from the electrical impedance system and convert them into a set of impedance values; 2) analyze the set of impedance values to determine a first time value indicating a first pulsatile component; 3) receive the second set of signals from the heart rate monitoring system and convert them into a set of cardiac rhythm values; 4) analyze the set of cardiac rhythm values to determine a second pulsatile component; 5) collectively process the first and second pulsatile components to determine a pulse transit time value; and 6) determine the blood pressure value by collectively processing the pulse transit time value and the blood pressure calibration value determined by the cuff-based system.

2. The system of claim 1, wherein the processing system further comprises computer code configured to: 1) calculate a mathematical derivative of the impedance values to determine a set of derivative values; and 2) determine a local maximum of the set of derivative values to determine the first pulsatile component.

3. The system of claim 1, wherein the processing system further comprises computer code configured to: 1) calculate a mathematical derivative of the impedance values to determine a set of derivative values; and 2) determine a zero-point crossing of the set of derivative values to determine the first pulsatile component.

4. The system of claim 1, wherein the processing system further comprises computer code configured to: 1) calculate a mathematical derivative of the impedance values to determine a set of derivative values; 2) estimate the set of derivative values with a mathematical function; and 3) analyze the mathematical function to determine the first pulsatile component.

5. The system of claim 1, wherein the processing system further comprises computer code configured to determine a local maximum of the cardiac rhythm values to determine the second pulsatile component.

6. The system of claim 1, wherein the cardiac rhythm values are representative of an ECG waveform.

7. The system of claim 6, wherein the processing system further comprises computer code configured to determine a QRS complex in the ECG waveform to determine the second pulsatile component.

8. The system of claim 7, wherein the processing system further comprises computer code configured to determine an R point in the QRS complex in the ECG waveform to determine the second pulsatile component.

9. The system of claim 7, wherein the processing system further comprises computer code configured to determine a Q point in the QRS complex in the ECG waveform to determine the second pulsatile component.

10. The system of claim 1, wherein the processing system further comprises computer code configured to further process the cardiac rhythm values to determine a heart rate value.

11. The system of claim 10, wherein the cardiac rhythm values are representative of an ECG waveform.

12. The system of claim 11, wherein the processing system further comprises computer code configured to determine a QRS complex in the ECG waveform.

13. The system of claim 12, wherein the processing system further comprises computer code configured to determine a first R point in a first QRS complex, and a second R point in a second QRS complex, and then determine a heart rate from a time interval separating the first and second R points.

14. A system for measuring a blood pressure value from a patient, comprising:
a base comprising a bottom surface configured to rest on or near a substantially horizontal surface, and a top surface configured to receive at least one of the patient's feet;
a cuff-based system, mounted directly on the base and configured to receive a foot from the patient, comprising an inflatable bladder configured to apply pressure to a portion of the foot and analyzes the applied pressure to determine a blood pressure calibration value;
an electrical impedance system connected to the top surface, the electrical impedance system comprising at least four electrodes, with a first electrode configured to inject an electrical current into the patient's feet, and a second electrode configured to measure a first set of signals induced by the electrical current and representative of a set of impedance values;
a heart rate monitoring system connected to the top surface and comprising a differential amplifier connected to an electrode that can be either the second electrode or a new, third electrode, the differential amplifier configured to measure a second set of signals representative of a set of cardiac rhythm values;
a weight-measuring system connected to the top surface, the weight-measuring system comprising an electrical system that measures a set of voltages that correlates with a force applied to the top surface; and
a processing system in electrical contact with the electrical impedance system and the heart rate monitoring system, and configured to: 1) receive the first set of signals from the electrical impedance system and convert them into a set of impedance values; 2) analyze the set of impedance values to determine a first time value indicating a first pulsatile component; 3) receive the second set of signals from the heart rate monitoring system and convert them into a set of cardiac rhythm values; 4) analyze the set of cardiac rhythm values to determine a second pulsatile component; 5) collectively process the first and second pulsatile components to determine a pulse transit time; and 6) determine the blood pressure value by collectively processing the pulse transit time value and the blood pressure calibration value determined by the cuff-based system.

15. The system of claim 14, wherein the electrical system comprises a Wheatstone Bridge.

16. The system of claim 15, wherein the Wheatstone Bridge connects electrically with an amplifier system.

17. The system of claim 16, wherein the processing system is further configured to receive the set of voltages, and analyze them to determine a value of weight corresponding to the force applied on the top surface.

18. The system of claim 14, wherein the processing system further comprises computer code configured to: 1) calculate a mathematical derivative of the impedance values to determine a set of derivative values; and 2) determine a local maximum of the set of derivative values to determine the first pulsatile component.

19. The system of claim 14, wherein the processing system further comprises computer code configured to: 1) calculate a mathematical derivative of the impedance values to determine a set of derivative values; and 2) determine a zero-point crossing of the set of derivative values to determine the first pulsatile component.

20. The system of claim 14, wherein the processing system further comprises computer code configured to: 1) calculate a mathematical derivative of the impedance values to determine a set of derivative values; 2) estimate the set of derivative values with a mathematical function; and 3) analyze the mathematical function to determine the first pulsatile component.

21. The system of claim 14, wherein the processing system further comprises computer code configured to determine a local maximum of the cardiac rhythm values to determine the second pulsatile component.

22. The system of claim 14, wherein the cardiac rhythm values are representative of an ECG waveform.

23. The system of claim 22, wherein the processing system further comprises computer code configured to determine a QRS complex in the ECG waveform to determine the second pulsatile component.

24. The system of claim 23, wherein the processing system further comprises computer code configured to determine an R point in the QRS complex in the ECG waveform to determine the second pulsatile component.

25. The system of claim 24, wherein the cardiac rhythm values are representative of an ECG waveform.

26. The system of claim 25, wherein the processing system further comprises computer code configured to determine a QRS complex in the ECG waveform.

27. The system of claim 26, wherein the processing system further comprises computer code configured to determine a first R point in a first QRS complex, and a second R point in a second QRS complex, and then determine a heart rate from a time interval separating the first and second R points.

28. The system of claim 23, wherein the processing system further comprises computer code configured to determine a Q point in the QRS complex in the ECG waveform to determine the second pulsatile component.

29. The system of claim 14, wherein the processing system further comprises computer code configured to further process the cardiac rhythm values to determine a heart rate value.

* * * * *